（12) United States Patent
Hussein

(10) Patent No.: US 12,216,017 B2
(45) Date of Patent: Feb. 4, 2025

(54) COMPLIANT TRI-AXIAL FORCE SENSOR AND METHOD OF FABRICATING THE SAME

(71) Applicant: Touchlab Limited, Edinburgh (GB)

(72) Inventor: Zakareya Hussein, Edinburgh (GB)

(73) Assignee: Touchlab Limited, Edinburgh (GB)

( * ) Notice: Subject to any disclaimer, the term of this patent is extended or adjusted under 35 U.S.C. 154(b) by 297 days.

(21) Appl. No.: 17/629,663

(22) PCT Filed: Jul. 22, 2020

(86) PCT No.: PCT/EP2020/070636
§ 371 (c)(1),
(2) Date: Jan. 24, 2022

(87) PCT Pub. No.: WO2021/013874
PCT Pub. Date: Jan. 28, 2021

(65) Prior Publication Data
US 2022/0252475 A1    Aug. 11, 2022

(30) Foreign Application Priority Data
Jul. 24, 2019    (GB) .................................... 1910563

(51) Int. Cl.
*G01L 5/162*    (2020.01)
*G01L 1/18*    (2006.01)

(52) U.S. Cl.
CPC ............. *G01L 5/162* (2013.01); *G01L 1/18* (2013.01)

(58) Field of Classification Search
CPC ......... G01L 1/205; G01L 5/167; G01L 5/162; G01L 5/228
See application file for complete search history.

(56) References Cited

U.S. PATENT DOCUMENTS 4,503,705 A * 3/1985 Polchaninoff ............. G01L 1/20
600/592
7,509,884 B2 * 3/2009 Morimoto ............... G01L 1/205
73/862.628
(Continued)

FOREIGN PATENT DOCUMENTS

CN    1796955 A    7/2006
CN    102414546 A    4/2012
(Continued)

OTHER PUBLICATIONS

Foreign Communication from a Related Counterpart Application, International Preliminary Report on Patentability dated Feb. 3, 2022, International Application No. PCT/EP2020/070636 filed on Jul. 22, 2020.
(Continued)

*Primary Examiner* — Tran M. Tran
(74) *Attorney, Agent, or Firm* — Conley Rose P.C.

(57) ABSTRACT

A compliant tri-axial force sensor is disclosed that may be incorporated into soft robots or electronic skin. The sensor comprises a first electrode layer including column electrodes in a first orientation; a second electrode layer including column electrodes in a second orientation that is orthogonal to the first orientation; a force-dependent active layer provided between the first electrode layer and the second electrode layer configured to change at least one property—such as quantum tunneling, conductivity, resistivity, or electrical charge—when subjected to a force; at least one three dimensional bump arranged to transmit externally applied force through the active layer; and at least one spacer arranged to maintain a separation between two or more layers in the sensor until an external force is applied.

15 Claims, 10 Drawing Sheets

(56) References Cited

U.S. PATENT DOCUMENTS

| | | | |
|---|---|---|---|
| 7,980,144 B2* | 7/2011 | Chang | G01L 1/205 |
| | | | 73/862.392 |
| 8,069,735 B1* | 12/2011 | Egorov | G01L 1/146 |
| | | | 73/862.041 |
| 8,564,397 B2* | 10/2013 | Kim | G01L 1/146 |
| | | | 338/114 |
| 9,347,838 B2* | 5/2016 | Chen | G01L 1/142 |
| 10,401,241 B2* | 9/2019 | Madden | G06F 3/04144 |
| 10,527,505 B2* | 1/2020 | Grau | G01L 1/2293 |
| 11,617,537 B2* | 4/2023 | Sarrafzadeh | A61B 5/7278 |
| | | | 702/41 |
| 11,971,317 B2* | 4/2024 | Grau | G01L 1/205 |
| 11,976,988 B2* | 5/2024 | Nohno | G01L 1/18 |
| 2009/0320611 A1* | 12/2009 | Vasarhelyi | B25J 13/084 |
| | | | 428/179 |
| 2012/0062245 A1 | 3/2012 | Bao et al. | |
| 2014/0150572 A1* | 6/2014 | Lim | G01L 5/228 |
| | | | 73/862.626 |
| 2017/0350772 A1* | 12/2017 | DeGanello | G01L 1/20 |
| 2019/0004651 A1 | 1/2019 | Hong et al. | |
| 2019/0113410 A1 | 4/2019 | Yoo et al. | |

FOREIGN PATENT DOCUMENTS

| | | |
|---|---|---|
| CN | 103954382 A | 7/2014 |
| CN | 108243620 A | 7/2018 |
| CN | 109946000 A | 6/2019 |
| JP | 2006250705 A | 9/2006 |
| JP | 2008209384 A | 9/2008 |
| JP | 2012173079 A | 9/2012 |
| JP | 2014085306 A | 5/2014 |
| WO | 2019034828 A1 | 2/2019 |
| WO | 2021013874 A1 | 1/2021 |

OTHER PUBLICATIONS

Foreign Communication from a Related Counterpart Application, Chinese Office Action dated Feb. 29, 2024, Chinese Application No. 202080066771.4.

Xiaoliang Chen, et al. "Flexible three-axial tactile sensors with microstructure-enhanced piezoelectric effect and specially arranged piezoelectric arrays" Smart Materials and Structures vol. 27, No. 2, pp. 2-22, Jan. 24, 2018.

Foreign Communication from a Related Counterpart Application, International Search Report and Written Opinion dated Oct. 21, 2020, International Application No. PCT/EP2020/070636 filed on Jul. 22, 2020.

Xiaoliang Chen, et al.: "Flexible three-axial tactile sensors with microstructure-enhanced piezoelectric effect and specially-arranged piezoelectric arrays", Smart Materials and Structures, IOP Publishing Ltd., Bristol, GB, vol. 27, No. 2, Jan. 24, 2018 (Jan. 24, 2018), p. 25018, XP020323919, ISSN: 0964-1726, DOI: 10.1088/1361-665X/AAA622.

Foreign Communication from a Related Counterpart Application, Japanese Office Action dated Jul. 2, 2024, Japanese Patent Application No. 2022-504585, filed on Jul. 22, 2020.

* cited by examiner

COMPLIANT TRI-AXIAL FORCE SENSOR AND METHOD OF FABRICATING THE SAME

CROSS-REFERENCE TO RELATED APPLICATIONS

The present application is a filing under 35 U.S.C. 371 as the National Stage of International Application No. PCT/EP2020/070636, filed Jul. 20, 2020, entitled "A COMPLIANT TRI-AXIAL FORCE SENSOR AND METHOD OF FABRICATING THE SAME," which claims priority to United Kingdom Application No. 1910563.4 filed with the Intellectual Property Office of the United Kingdom on Jul. 24, 2019, both of which are incorporated herein by reference in their entirety for all purposes.

FIELD OF THE INVENTION

The present invention relates to a compliant tri-axial force sensor and method of fabricating such a sensor.

BACKGROUND OF THE INVENTION

For robots and machines to be able to interact with the world around them in a similar way to human beings, they must also have a highly sensitive sense of touch similar to human beings. One of the most difficult areas to imitate in a robot is the palm of the hand, as it has one of the highest densities of nerve receptors in the human body. Furthermore, skin has multiple mechanoreceptors for sensing different forces/pressures as well as vibrational frequencies. Static sensing of pressure is of most interest for the ability of robots to handle delicate objects. To this end, multiple tactile sensors have been made to provide pressure data.

The majority of sensors currently in the market consist of individual force sensors or other sensors. These only provide a scalar value for pressure across what can be considered a relatively large surface area. Others that provide more advanced haptic information include sensors that are robust but require replacing an entire robot finger.

However, force is a vector with two components, its magnitude as well as direction. Directional information/data has been of high interest in improving robotics for many years. A sensor that can determine both magnitude and direction is usually referred to as a tri-axial force sensor. These force torque (F/T) sensors are largely used as part of a robotic end-effector arm (see reference 1 listed at the end of the description), or more recently to measure the force directional components on robot finger-tips (see reference 2 listed at the end of the description). Many attempts have historically been made for such sensors, the more recent ones of which have achieved relatively high densities, however they have been made using solid-state materials and/or micromachining techniques. Not only is the force readout sensitive to bending around a given surface, many of them cannot be bent and can only be integrated into hard robots. More recently, the need for compliant tactile systems has been realised both for human as well as robot monitoring. Many of these compliant/conformable pressure-sensing systems can be classified as a type of electronic skin (e-skin).

Some recent e-skins and data gloves have been made with the ability to give multiple points or high density tactile information (see references 3 and 4 listed at the end of the description), however most cannot give directional information which is crucial to measuring many phenomena. It can enable robots to grasp objects, detect their mass in a gravitational environment such as the earth, but also, for example, to measure ground reaction force in insoles for gait analysis, among other physical phenomena.

Recently, many attempts have been made to make fully compliant tri-axial force sensors. Various esoteric methods have been used for this including various designs of compliant strain-gauges using liquid metals such as eGaIn (eutectic gallium indium) (see reference 5 listed at the end of the description) with some designs similar to Rosette strain gauges, which are difficult to manufacture and may cause toxic leakage, and others being bulky pneumatic chamber based sensors, and self-adjusting Carbon Nanotube (CNT) arrays.

When it is desired to integrate any of these sensing systems with a high density, a matrix array is necessary as it reduces wiring considerations and hence the space these take up on the e-skin. Although this has been done to a large extent with capacitive sensing whether with metal, conductive liquid, or otherwise (see references 6, 7 and 8 listed at the end of the description), this type of sensing is sensitive to the substrate it is used on (e.g. human skin, metal robot) due to capacitive coupling that can occur with the surface and the sensor. Furthermore, capacitive sensing requires complex readout electronics, and is susceptible to background electromagnetic (EM) noise, making it impractical for many applications. Other methods have also been used, but all suffer from certain drawbacks; piezoelectric sensing (see reference 9 listed at the end of the description), with the potential ability for actuation as well as detection (see reference 10 listed at the end of the description), is susceptible to significant background electromagnetic compatibility (EMC) noise and is unable to perform static sensing; magnetic sensing (including the hall-effect and inductive methods) (see references 11 to 14 listed at the end of the description) is also affected by background EMC and surrounding magnetic fields, some of which could be created by the robot's own actuators.

Additionally, it is of paramount importance to make the e-skin as thin as possible for it not to interfere with the device on which it is to be retrofitted, while also having a compact electronics readout system, something most solutions/systems are lacking. A highly promising but somewhat expensive fabrication process was recently developed whereby self-adjusting carbon nanotube arrays are used to readout tri-axial information in integrated arrays that are grown on side-walls during the fabrication process, with excellent cycling repeatability (see reference 15 listed at the end of the description).

Quantum tunnelling materials as well as piezoresistive composites have been used before, but none of the systems proposed have been highly integratable or wrappable. Often flexible wiring is not flexible or compliant enough, either due to the material being too rigid or compliant in only 1-axis, or the layers not being thin-enough. The architecture for such a device usually involves the placement of a 'bump' that translated force into torque being placed directly above 4 orthogonally arranged pressure sensors or pressure sensing pixels (sensels). When the post experiences a force from a given direction at its tip, this gets translated into downwards force as well as a sideways torque. Consequently, the 4 pressure sensors experience different forces/pressures. Measuring the quantity of resistance change on each of these sensors can then be used to dissect the force into its 3D Cartesian components ($F_x$, $F_y$ and $F_z$). Various electrode configurations may be used for reading out the signal from the piezoresistive material (see reference 16 listed at the end of the description).

To date, the closest anyone has come to making piezoresistive tri-axial sensor arrays include an interlocked structure with sidewalls embedded in polydimethylsiloxane (PDMS) and a micro-pyramidal array structure (see reference 17 listed at the end of the description). The former has the advantage of being able to be deployed in relatively dense 3×3 arrays, however only works at very low loads of 0-225 Pa. The latter has the advantage of having a wide dynamic range from 128 Pa to 44 kPa. However, it needs a high quantity of wiring as it is not amenable to be deployed as a matrix, while also having an overall structure which is several millimetres thick, meaning it cannot be wrapped around surfaces, and due to its complexity, mass-production would be very difficult.

Quantum Tunnelling Composite (QTC®) materials were discovered in 1996 by David Lussey. They are composite materials composed essentially of metal particles as well as a non-conducting elastomeric binder or matrix. These materials have a very high resistance to electrical current, and are essentially insulators, when no pressure is applied. Once pressure is applied, their resistance drops exponentially, and this can be measured using the correct electrical circuitry. The reason for this is that the metal particles are dispersed in the material at a particular concentration, but are not in physical contact with one another. Upon the application of pressure, the metal particles approach each together, and despite not being able to touch each other, electrons begin to be able to jump from one particle to another through a phenomenon known as quantum tunnelling. The higher the pressure, the closer the particles get to one another, which in turn increases this tunnelling effect and reduces the resistance of the material. In order for this to work well, a good dispersion of the particles within the binder is necessary, as well as their small size, as tunnelling only takes effect on small scales. For this reason particles are usually micrometre or nanometre sized and made up of a conductive material, typically a metal such as silver, gold, or magnetite. They are also often nano-patterned, and for example 'spiky' nanoparticles show better tunnelling behaviour than round ones, as the tips of the microscopic spikes enhance tunnelling current even if particles are at a higher distance from each other. This enhances sensitivity and overall performance.

QTC® pills supplied by Peratech have been used in an attempt to make tri-axial sensors but these devices suffer from miniaturization and other issues such as sensor hysteresis. QTC® pills lack the ability to be integrated during a mass manufacturing process and are bulky in both thickness and minimum diameter, making them cumbersome and not particularly sensitive.

To summarise, commercial flexible force sensors on the market only give a scalar value for force, but not its direction or shear forces. They are not capable of withstanding significant flexing, while also changing their value during flexing. Furthermore, array technology, including tri-axial technology is required in order to get the necessary data to enable multiple advanced applications. This is particularly important in e.g. gait analysis of humans and robots which need to measure ground reaction force, robots manipulating objects in a complex manner, robots handling delicate objects without damaging them, monitoring physiological forces such as muscle activity and blood flow on humans with wearable garments, sensing flow phenomena of fluids such as air or water on top of tidal and wind turbines, allowing surgeons to 'palpate' tissues with surgical robots, etc.

Compliant Tri-axial sensors can be created (in research labs) using multiple transduction mechanisms such as: piezoresistive (e.g. using strain gauges or nanocomposites); capacitive; piezoelectric; inductive; optical; or magnetic. Piezoresistive and capacitive sensors dominate due to their excellent performance. However, capacitive sensors can be sensitive to the substrate they are placed on due to capacitive coupling with this surface, and require much more complex readout electronics which is a hindrance due to space requirements and implementation complexity. Drawbacks of the other sensors include: piezoelectric sensors cannot sense static contact force since the induced charge in the material dissipates very quickly; most of these sensors are sensitive to temperature, and are generally not robust; there is a lack of dynamic force sensing range; EMC noise-sensitive (especially in magnetic and piezoelectric sensors); some piezoelectric sensors are light-sensitive. In addition, most known processes for making these sensors are inherently low-yield, inconsistent and not scalable. Often, measurements with such sensors are not repeatable making the sensors unreliable.

Of all the sensors available, none are robust-enough to function in a desirable manner when in real-world settings. There is an urgent need in industry for a robust sensor, with durable materials which can withstand thousands to millions of cycles, is insensitive to temperature and harsh environmental conditions, and which can perform tri-axial force sensing. The sensor must also be extremely thin so that it can be added to existing devices without disturbing their functioning, and the working of the sensor should be insensitive to bending so that it can also function on soft surfaces such as soft robots or human skin.

It is therefore an aim of the present invention to provide a compliant tri-axial force sensor and method of fabricating such a sensor, which addresses at least some of the problems discussed above with the current technology.

SUMMARY OF THE INVENTION

In a first aspect of the present invention, there is provided a compliant tri-axial force sensor comprising:
- a first electrode layer having an array of column electrodes in a first orientation;
- a second electrode layer having an array of column electrodes in a second orientation, which is orthogonal to the first orientation;
- a force-dependent active layer which is configured to change at least one property when subjected to a force and which is provided between the first electrode layer and the second electrode layer;
- at least one three dimensional bump arranged to transmit externally applied force through the active layer; and
- wherein at least one spacer is provided which is arranged to maintain a separation between two or more layers in the sensor until an external force is applied.

Thus, embodiments of the invention comprise a compliant tri-axial force sensor which can be made of thin material layers allowing it to be fully compliant and flexible but which includes one or more spacers to maintain a spacing between certain layers such that the bending of the sensor will not itself cause erroneous force readings and the sensor can therefore be robust, reliable and repeatable. Thus, the sensor can tolerate thousands to millions of cycles without failing, and can therefore effectively operate in an industrial setting. A consistent output also eliminates significant time which may otherwise be required to calibrate each sensing element individually. This is especially useful in some embodiments which employ 4 sensels (sensing elements) per tactel (tactile element), i.e. bump. In addition, the sensor has a low susceptibility to background noise and can be easily configured for different force sensing ranges depending on the application (i.e. by increasing or decreasing the active layer thickness).

Advantageously, the sensor may be configured to be a thin, stretchable, conformable, nanocomposite-based tactile device which can measure force in three different axes (x, y and z). Embodiments of the invention may be compliant-enough to be wrapped around extremely small bending radii or soft robots, and nonetheless have a minimal effect on signal integrity or response allowing an accurate measurement of force magnitude as well as direction. Accordingly, the sensor performance is insensitive to bending. Flexible connections and electrical wiring is integrated into the sensor via the layer and electrode structure, and it has a 'bump' layer on top which translates force into torque. In addition, the sensor is amenable to mass-production using any of a number of existing facile volume manufacturing processes such as screen printing and roll-to-roll printing using customizable materials whilst maintaining high yield. Thus, it can be deployed in large-scale arrays such as may be required for an electronic skin application. Currently, no general purpose electronic skin of this type exists. The sensor is highly integratable into different devices, products or garments and can be retro-fittable onto hard, soft, and stretchable surfaces. Moreover, environmentally friendly materials may be employed.

Each layer may be printed (e.g. by screen printing or inkjet printing) allowing it to be highly miniaturisable (at least to an ideal 1 mm by 1 mm tri-axis pixel density desired for a robotic end-effector). In some embodiments, the first and/or second electrode layer may be formed from a conductive ink deposited on a layer below.

All of the above advantages enable embodiments of the invention to provide a commercially viable sensor suitable for 'real-world' industrial applications outside of a controlled lab environment or academia.

The active layer may comprise at least one of: a quantum tunneling material, a piezoresistive material or a piezoelectric material. Thus, the at least one property that may change when the active is subjected to a force is the amount of: quantum tunnelling; conductivity; resistivity or electrical charge. Accordingly, embodiments of the invention may employ a composite material that utilises a quantum tunnelling conduction mechanism or piezoresistive conduction mechanism to translate applied force into a sensed signal. The active layer is conveniently anisotropic such that it reacts more selectively to normal forces when deposited in a thin layer, due to the material properties.

The at least one three dimensional bump may have a footprint which extends at least partially over at least two column electrodes in the first electrode layer and at least partially over at least two column electrodes in the second electrode layer such that forces applied to the bump are transmittable through the active layer in at least four discrete regions. In this way, each tactel (tactile element) is connected to 4 sensels (sensing elements) or pixels and the strength of the force at each sensel can be used to determine both the magnitude and direction of the applied force (i.e. resulting in a combination of shear and compressive forces).

In other embodiments, the at least one three dimensional bump has a footprint contained within a space between two column electrodes in the first electrode layer and between two column electrodes in the second electrode layer. In this case, one or more spacers can be employed to redistribute the force applied to the bump to each of the 4 sensels (sensing elements).

The active layer may comprise a first active layer and a second active layer with a gap there-between.

The sensor may comprise one or more of: a base layer below the first electrode layer; a top layer above the second electrode layer; a first carbon layer between the first electrode layer and the active layer; a second carbon layer between the second electrode layer and the active layer; and a cover layer over the at least one three dimensional bump.

The first and/or second carbon layer may be continuous across multiple column electrodes in the first and/or second electrode layer.

The at least one spacer may be provided within the active layer; between the base layer and the top layer; or on or through the first or second electrode layer.

The at least one spacer may be in the form of a dot, a column, a post, a cylinder, a tubular, a pyramid or a mesh.

The at least one spacer may have a solid or hollow transverse cross-section in the form of a circle, square, rectangle, diamond, pentagon, hexagon or honeycomb lattice.

The sensor may comprise an array of said spacers. The spacers in the array may have a plurality of different dimensions.

The active layer may form a continuous layer across multiple column electrodes in the first and/or second electrode layer.

The active layer may form a discontinuous layer across the column electrodes in the first and/or second electrode layer.

The sensor may comprise an insulator between adjacent electrodes in the first and/or second electrode layer.

The at least one spacer may take the form of a binder provided between the active layer and the first and/or second electrode layer, wherein the binder is provided in gaps between adjacent column electrodes and extends between the active layer and respective edges of said adjacent column electrodes.

The sensor may comprise an adhesive layer provided between one or more adjacent layers.

The at least one three dimensional bump may comprise a polymer having a different elasticity to a remainder of the sensor.

The at least one three dimensional bump may be in the form of a mesa, dome, hemisphere, hemispherical section, cone, cone section, cuboid, cylinder, half-cylinder, pyramid, pyramid section, tetrahedron, tetrahedron section, hexahedron, triangular prism, polyhedron, or other shape.

The at least one three dimensional bump may have a height that is at least twice a height of a remainder of the sensor. In some embodiments, the bumps may be significantly taller than the remainder of the sensor (e.g. up to 3 mm in height) in order to translate shear forces into a high enough torque, which in turn compresses the active layer material underneath with different pressures. In some embodiments, the active layer may have a width of 1 mm between electrodes and each tactel may be composed of 4 pixels in a matrix array, each with 2 mm spacing, such that the sensing area is 3 mm×3 mm=9 mm$^2$. However, with a more sensitive active layer, a better resolution may be obtained. Spacing between the tactels and sensels can be very low to increase resolution (e.g. 500 µm or below), as long as they are not touching and tunnelling cannot occur between them. Separating electrodes in this way helps to reduce cross-talk in the sensor.

The sensor may comprise an array of said three dimensional bumps.

In accordance with a second aspect of the invention there is provided a method of fabricating a sensor according to the first aspect described above, comprising:

providing a first electrode layer having an array of column electrodes in a first orientation;

providing a second electrode layer having an array of column electrodes in a second orientation, which is orthogonal to the first orientation;

providing a force-dependent active layer which is configured to change at least one property when subjected to a force and which is provided between the first electrode layer and the second electrode layer;

providing at least one three dimensional bump arranged to transmit externally applied force through the active layer; and providing at least one spacer which is arranged to maintain a separation between two or more layers in the sensor until an external force is applied.

Thus, embodiments of this aspect of the invention provide a method fabricating a sensor which can easily be mass-produced using a variety of existing techniques.

Each layer, bump or spacer may be provided by one of: printing; screen-printing, roll-to-roll printing, inkjet printing, 3D printing, electrospinning, depositing, droplet dispensing, casting, coating, moulding, spinning or weaving.

The method may comprise forming at least the first electrode layer and the second electrode layer on a single substrate; separating the substrate into two parts; and stacking the two parts together.

The method may comprise forming the at least one spacer on at least one part prior to said separating and/or stacking.

BRIEF DESCRIPTION OF THE DRAWINGS

Non-limiting embodiments of the invention will now be described for the sake of example only, with reference to the following drawings in which.

DETAILED DESCRIPTION OF THE EMBODIMENT

Figure 1A:
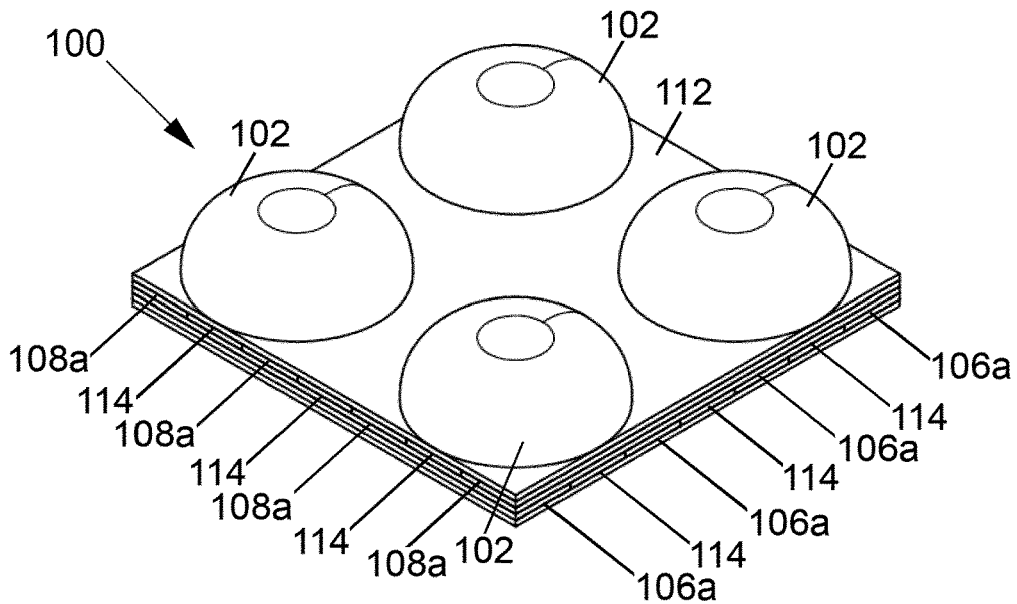
FIG. 1A shows a top perspective view of a compliant tri-axial force sensor including a dome-shaped bump in accordance with a first embodiment of the invention.

In accordance with FIGS. 1A, B and C there is shown a compliant tri-axial force sensor 100 including four three dimensional dome-shaped bumps 102 in accordance with a first embodiment of the invention. The sensor 100 comprises a base layer 104 in the form of a bottom membrane encapsulation layer; a first (bottom) electrode layer 106 having an array of column electrodes 106a in a first orientation; a second (top) electrode layer 108 having an array of column electrodes 108a in a second orientation, which is orthogonal to the first orientation; a force-dependent active layer 110 in the form of a quantum tunneling material layer, which is configured to change at least one property when subjected to a force and which is provided between the first electrode layer 106 and the second electrode layer 104; and a top layer 112 in the form of a top membrane encapsulation layer. The dome-shaped bumps 102 are provided on the top layer and are arranged to transmit externally applied force through the active layer 110. Although not shown in FIGS. 1A, B and C, at least one spacer is provided which is arranged to maintain a separation between two or more layers in the sensor 100 until an external force is applied. The spacers will be described in more detail below in relation to FIGS. 4 through 110.

Figure 1B:
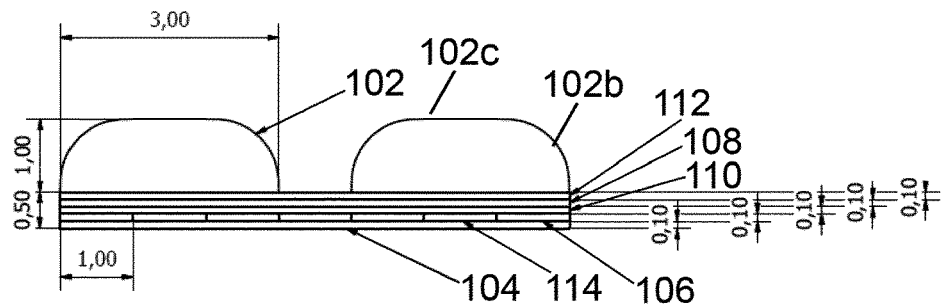
FIG. 1B shows side view of the sensor of FIG. 1A.

As shown in FIGS. 1A and 1B, an optional array of insulation 114 is provided in-between the column electrodes 106a in the first electrode layer 106. A similar array of insulation 116 is also provided in-between the column electrodes 108a in the second electrode layer 108. Each bump 102 has a circular base 102a and curved sidewalls 102b which extend to a flattened top 102c.

In this embodiment, each of the base layer 104, the first electrode layer 106, the active layer 110, the second electrode layer 108 and the top layer 112 are 0.10 mm thick forming a sensor body of 0.50 mm thick. Furthermore, each column electrode 106a, 108a is 1 mm wide and each bump 102 is 1 mm in height and has a maximum diameter footprint of 3 mm. There is a 1 mm gap between each adjacent bump 102. In other embodiments, other dimensions may be used to suit particular applications. However, it is envisaged that the sensor body will usually be formed of relatively thin layers to allow the sensor to be compliant and to be capable of being applied to curved or other shaped surfaces. As shown here, in some embodiments, the bumps 102 may be significantly taller than the sensor body in order to translate shear forces into a high enough torque, which in turn compresses the active layer 110 underneath with different pressures.

Figure 1C:
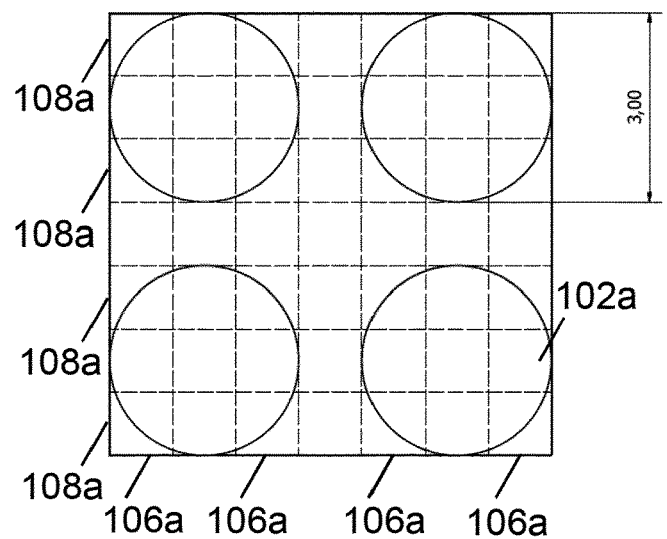
FIG. 1C shows a plan view of the sensor of FIG. 1A.

As shown in FIG. 1C, each three dimensional dome-shaped bump 102 has a footprint which extends at least partially over at least two column electrodes in the first electrode layer 106 and at least partially over at least two column electrodes in the second electrode layer 108 such that forces applied to the bump 102 are transmittable through the active layer 110 in at least four discrete regions. In this way, each bump 102 can be considered as a tactile element (tactel) which is connected to four sensing elements (sensels) or pixels and the strength of the force at each sensel can be used to determine the position, magnitude and direction of the applied force (i.e. resulting in a combination of shear and compressive forces) as will be explained further below, with reference to FIGS. 12A, B and C. Note, in FIG. 1C the column electrodes 106a, 108a are shown in dashed lines as if the layers of the sensor 100 are transparent.

Although the sensor 100 is shown with an array of four bumps 102, the sensor body may be extended and may comprise any number of bumps 102 as required for any given application.

In any of the embodiments described, the sensor may be formed from any selection of the materials listed below.

The base layer 104 and top layer 106 may be formed from any suitable substrate material and may comprise one or more of Poly(para-xylelene) polymers (Parylene), 2,8-Dichlorotricyclo[8.2.2.2$^{4,7}$]hexadeca-1(12),4,6,10,13,15-hexaene (Parylene-C), Polydimethylsiloxane (PDMS), Polyimide (PI), polybutyrate adipate terephthalate (polybutyrate), Poly(methyl methacrylate) (PMMA/Acrylic), prop-2-enoates (acrylate), polyethylene (PE), High-density polyethylene (HDPE), Low-density polyethylene (LDPE), Polyethylene Terephthalate (PET), Thermoplastic Polyurethane (TPU), Polyurethane (PU), Polysiloxanes (Silicone), Polyvinyl Chloride (PVC), Polyethyleneimine (PEI), Polyethylene Naphthalate (PEN), Polypropylene (PP), Polystyrene (PS), aliphatic or 30 semi-aromatic polyamide (PI), Polytetrafluoroethylene (PTFE), Polyvinylidene fluoride (PVDF), non-woven fabric or a blend thereof. Low Young's modulus polymers may help to attain higher conformability, such as those polymers having a Young's modulus of up to 1.5 MPa (Mega-Pascals), more preferably up to 1.2 MPa, still more preferably up to 1 MPa and preferably at least 500 kPa, such as in the range 700 kPa to 1 MPa, e.g. 700 to 800 kPa. This applies particularly to PDMS; the downside to these low Young's modulus polymers is that they are often too fragile or not heat-resistant enough for some applications. For this reason a blend such as TPU coated silicone may be used. Many more rigid polymers in the list (e.g. PEN) are highly flexible at a thickness of e.g. 25 microns. Some example thicknesses for different possible substrates are: Parylene-C, 500-10000 nm; PEN, 25-100 microns; PET, 36-125 microns; Silicone, 5-500 microns; and TPU, 50-75 microns.

The column electrodes 106a, 108a of both the first electrode layer 106 and the second electrode layer 108 may be formed of a conductive composite material such as an ink containing metal filler particles (micro or nanoscale). Carbon, silver, gold, and copper are the most commonly used. Metal thin-film (e.g. gold/copper) can be used if the substrate is not stretchable or particularly thin, or if the metal has tortuosity to bend while the substrate is being stretched, instead of stretching the metal itself. All of these need to be highly conductive, and the best metal to be used is gold due to it being the most malleable and ductile of all metals. Some example materials that may be used for the column electrodes 106a, 108a are conductive inks (CI) by Engineered Materials Solutions, Inc. (EMS) (e.g. CI-1036 which is a silver conductive ink having a sheet resistivity of <0.010 Ω/square at 25.4 microns thickness; or CI-2051 which is a carbon-based conductive ink having a sheet resistivity of <50 Ω/square at 25.4 microns thickness). Other suitable materials include Asahi™ ink and gold thin-film which has a resistivity of ~2.44×10$^{-8}$ Ωm at 20 degrees Celsius.

The active layer 110 may comprise a quantum tunneling material, a piezoresistive material or a piezoelectric material. The quantum tunnelling material will exhibit an exponential decrease in resistance due to quantum tunnelling which leads to a massive resistance change up to $10^{12}\Omega$, spanning a very large dynamic force range. In some embodiments, the force range that can be sensed can be as low as 0.003N up to 200N and if more rigid materials are used in the sensor this could be expanded higher. An example of a suitable quantum tunneling material is Quantum Tunneling Composite (QTC®) which comprises a binder material plus nickel or silicon (semiconductor) filler particles with high aspect ratio tips (e.g. circular, spiky, or needle-like). Particles composed of dielectric materials such as titanium dioxide or fumed silica particles may also be used in the material. Metal or metal-alloys having a void bearing structure may also be used along with various different binders. Another suitable quantum tunneling material is QTSS® which contains spiky or acicular magnetite and/or nickel particles and polyurethane binder. The particles do not touch each other but current can pass through them by means of the mechanism of quantum tunnelling. Zero dimension, one dimension, or two dimension nanoparticle materials may be desirable due to their enhanced dynamic range and sensitivity. Part of the reason for this may be due to local concentration of electric fields at their tips enhancing quantum tunnelling as well as a lower percolation threshold (and hence quantity) of the materials required. Advantageously, quantum tunnelling materials are most sensitive to compressive pressure between the electrodes measuring the resistance, which allows significant selectivity not provided by, for example, strain gauges. Quantum tunnelling materials are also less sensitive to temperature and environmental electromagnetic compatibility noise than many other sensors and materials.

Suitable piezoresistive materials include nanocomposites and electrospun micro or nanofibers. Piezoresistive materials modulate current flow when a potential different is applied across them and pressure is applied to the material. These comprise an active filler (micro/nanoparticle) which may be carbon, carbon nanotube (CNT), multi-walled carbon nanotube (MWCNT), graphene, Borophene, silver, quantum dots, or any other electrically conductive or semiconductor micro/nanoparticles. They may also comprise surfactants which are usually functionalised on the surface of the nanoparticles to increase dispersion and reduce agglomeration due to e.g. Van der Waals forces. A binder is also employed such as PDMS, silicone, tetrafluoroethylene (TFE), Propylene, PVDF (which is not piezoelectric in all its states), other polymers such as the ones contained in the substrate or concrete. The polymers can be thermosetting (i.e. undergo a permanent cross-linking reaction due to heat, moisture, light, or air) or non-thermosetting (i.e. melting). They can also be fluoropolymers. The piezoresistive materials may also comprise a solvent to control viscosity (e.g. during printing) but which is usually mostly evaporated away in air or while curing. The nanoparticles are ideally vertically aligned (and well dispersed) in order to enhance the anisotropic behaviour of the material to sense pressure in the normal direction with minimal pressure readout due to the material flexing and stretching. Some particles in the piezoresistive material may be electrically or magnetically aligned (by application of a static or varying electric and/or magnetic field across the materials before and/or during curing and/or deposition). For example, this can be done using dielectrophoretic alignment by varying an AC (alternating current) electric field through the material before curing, DC (Direct-Current) alignment by applying a DC current through the material, or purely by a DC Electric Field where a static field is present in the material without a current travelling through its conductive particles. This alignment can be done to make the piezoresistive material more anisotropic or optically transmissive. If the conductive particles in the piezoresistive material themselves do not respond to the applied fields, they may be functionalized with other nanoparticles (e.g. iron-oxide nanoparticles which are ferromagnetic) in order to be aligned. Other potentially suitable piezoresistive materials include thin-films of any of the fillers used in the nanocomposites listed above.

Suitable piezoelectric materials also include nanocomposites and electrospun micro or nanofibers. These may comprise an active filler (micro-/nanoparticle) that exhibits a charge separation due to an external stress, and which may include but is not limited to Zinc-Oxide (ZnO), Polyvinylidene Fluoride (PVDF), poly[(vinylidenefluoride-co-trifluoroethylene] [P(VDF-TrFE)], Lead Zirconate Titanate (PZT), Barium Titanate (BaTiO$_3$), Lead (II) Titanate (PbTiO$_3$), Lithium Tantalite (LiTaO$_3$), Aluminium Nitride (AlN), Boron-Silicate Mineral with compounded elements (Tourmaline), Lead Magnesium Niobate-Lead Titanate (PMN-PT) or any combination thereof plus a binder such as those listed above. Other potentially suitable piezoelectric materials include thin-films of any of the fillers used in the nanocomposites listed above.

The bumps 102 may comprise a polymer such as a dielectric polymer, a polysiloxane, rubber, silicone, or an amorphous crystalline material such as glass.

Figure 2A:
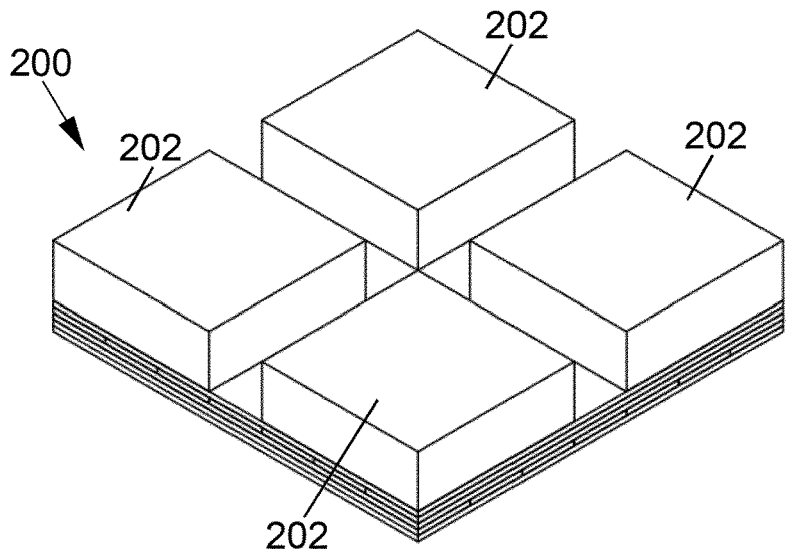
FIG. 2A shows a top perspective view of a compliant tri-axial force sensor including a cubic-shaped bump in accordance with a second embodiment of the invention.
Figure 2B:
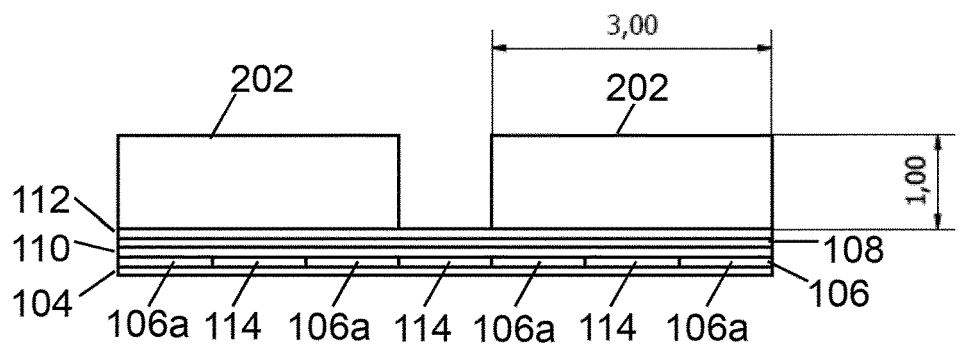
FIG. 2B shows side view of the sensor of FIG. 2A.
Figure 2C:
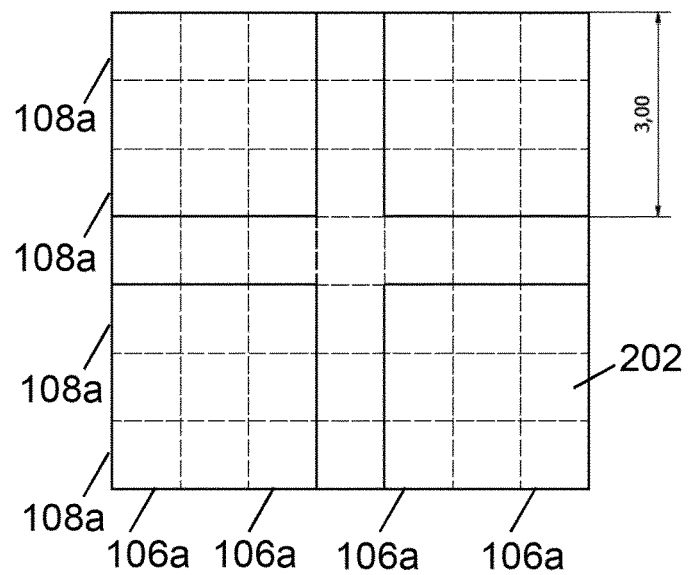
FIG. 2C shows a plan view of the sensor of FIG. 2A.

FIGS. 2A, B and C show a compliant tri-axial force sensor 200 including four three dimensional cuboid bumps 202 in accordance with a second embodiment of the invention. The sensor 200 comprises a sensor body identical to that described above for sensor 100 but with the four dome-shaped bumps 102 replaced with four cuboid bumps 202. Like reference numerals will therefore be used for like parts. As above, the bumps 202 each have a footprint which extends over two column electrodes 106a in the first electrode layer 106 and over two column electrodes in the second electrode layer 108 such that forces applied to the bump 202 are transmittable through the active layer 110 in at least four discrete regions.

Figure 3A:
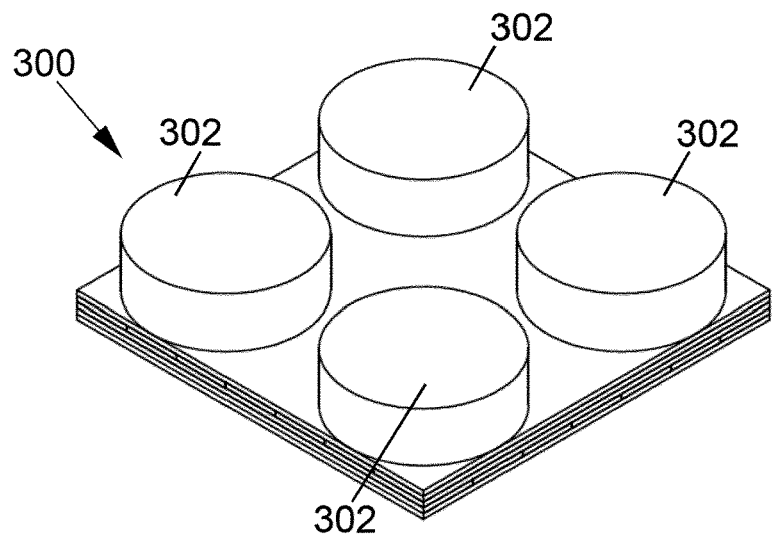
FIG. 3A shows a top perspective view of a compliant tri-axial force sensor including a cylindrical-shaped bump in accordance with a third embodiment of the invention.
Figure 3B:
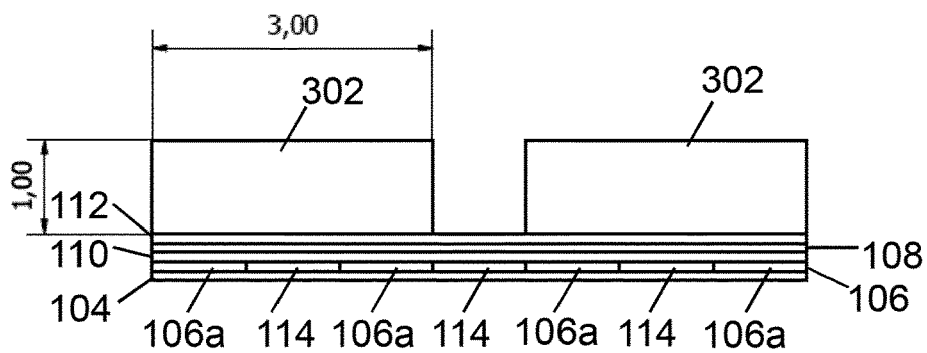
FIG. 3B shows side view of the sensor of FIG. 3A.
Figure 3C:
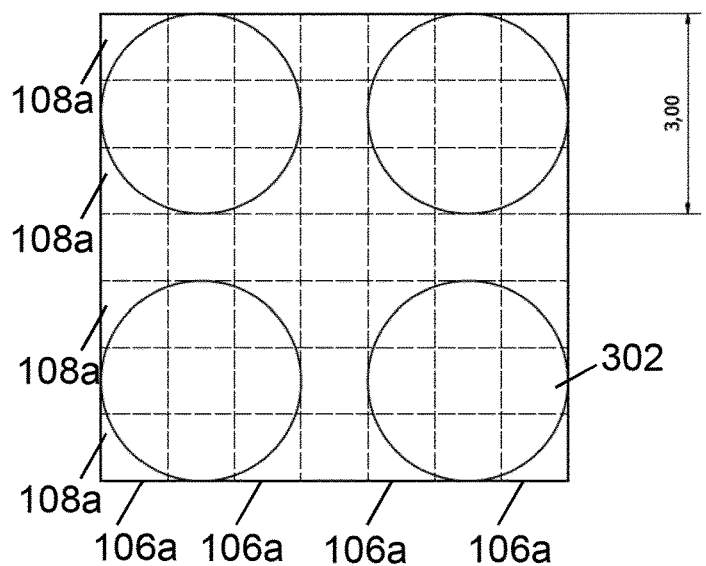
FIG. 3C shows a plan view of the sensor of FIG. 3A.

FIGS. 3A, B and C show a compliant tri-axial force sensor 300 including four three dimensional cylindrical bumps 202 in accordance with a third embodiment of the invention. The sensor 300 comprises a sensor body identical to that described above for sensor 100 but with the four dome-shaped bumps 102 replaced with four cylindrical bumps 302. Like reference numerals will therefore be used for like parts. As above, the bumps 302 each have a footprint which extends over two column electrodes 106a in the first electrode layer 106 and over two column electrodes in the second electrode layer 108 such that forces applied to the bump 302 are transmittable through the active layer 110 in at least four discrete regions.

It will be understood that the three dimensional bumps described above are only examples and in other embodiments, each bump may be in the form of a mesa, dome, hemisphere, hemispherical section, cone, cone section, cuboid, cylinder, half-cylinder, pyramid, pyramid section, tetrahedron, tetrahedron section, hexahedron, triangular prism, polyhedron, or other shape. Furthermore, a sensor may comprise bumps of different shapes and/or materials to suit any given application.

Figure 4:
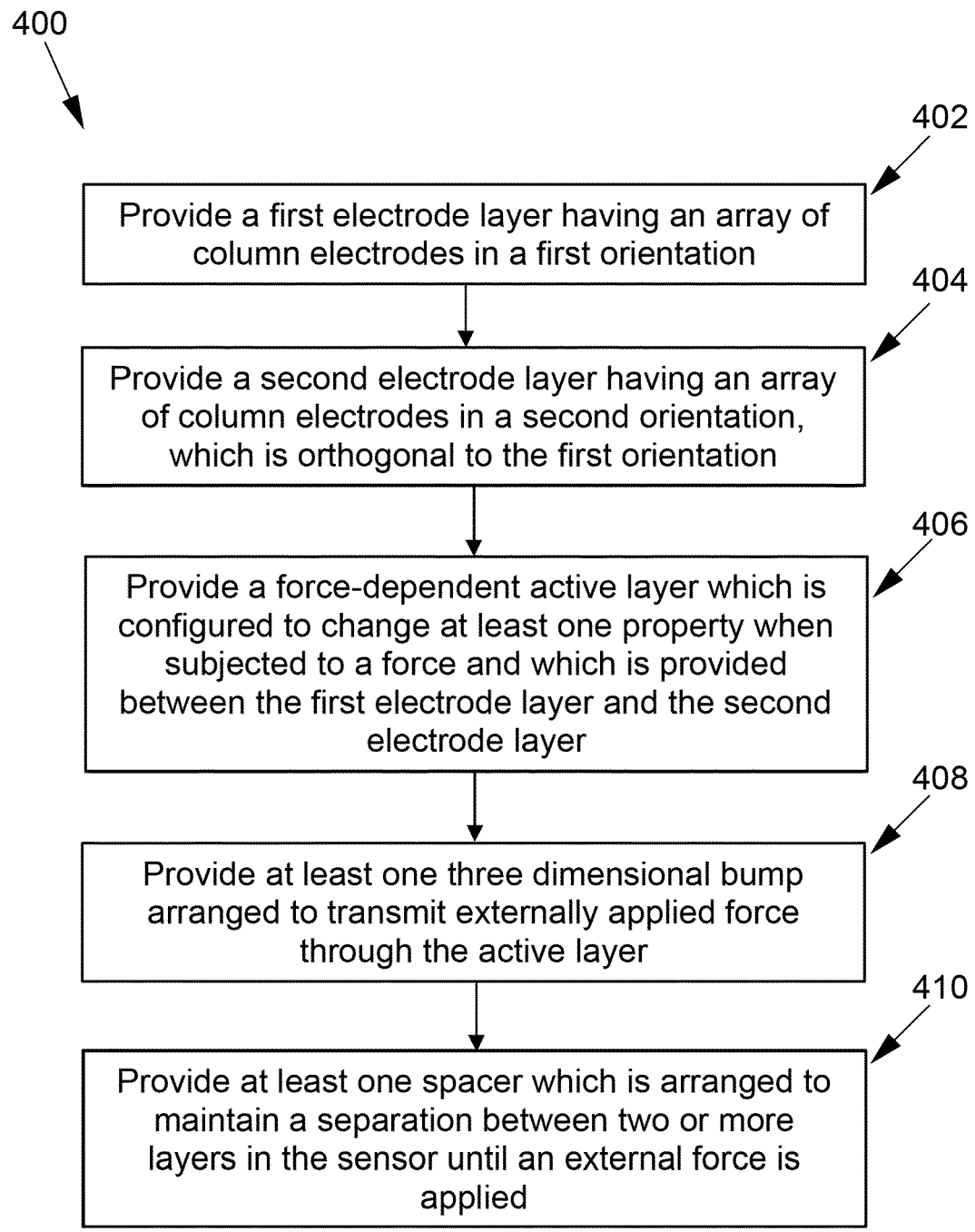
FIG. 4 is a flow chart of a method of fabricating a sensor according to an embodiment of the invention.

FIG. 4 is a flow chart of a general method 400 of fabricating a sensor such as those described above, according to an embodiment of the invention. The method 400 comprises step 402 of providing a first electrode layer 106 having an array of column electrodes 106a in a first orientation; a step 404 of providing a second electrode layer 108 having an array of column electrodes 108a in a second orientation, which is orthogonal to the first orientation; a step 406 of providing a force-dependent active layer 110 which is configured to change at least one property when subjected to a force and which is provided between the first electrode layer 106 and the second electrode layer 108; a step 408 of providing at least one three dimensional bump 102, 202, 302 arranged to transmit externally applied force through the active layer 110; and a step 410 of providing at least one spacer which is arranged to maintain a separation between two or more layers in the sensor until an external force is applied. As above, the spacers will be shown and described in more detail below.

Each layer, bump or spacer may be provided by one of: printing, screen-printing, roll-to-roll printing, inkjet printing, 3D printing, electrospinning, depositing, droplet dispensing, casting, coating, moulding, spinning or weaving. The method 400 may comprise forming at least the first electrode layer 106 and the second electrode layer 108 on a single substrate 104; separating the substrate into two parts; and stacking the two parts together as will be explained in further detail below. The method 400 may also comprise forming the at least one spacer on at least one part prior to said separating and/or stacking.

Figures 5A, 5B:
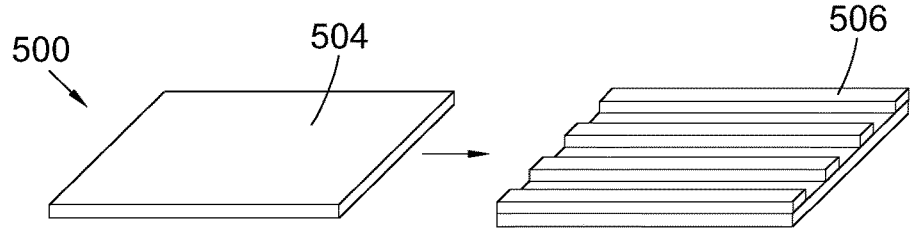
FIG. 5A to 5I illustrate the steps of a method of fabricating a sensor according to another embodiment of the invention.
Figures 5C, 5D:
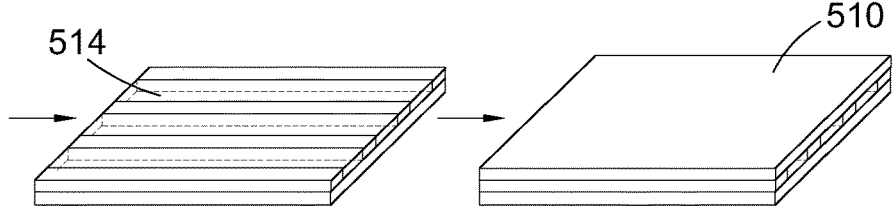
Figures 5E, 5F:
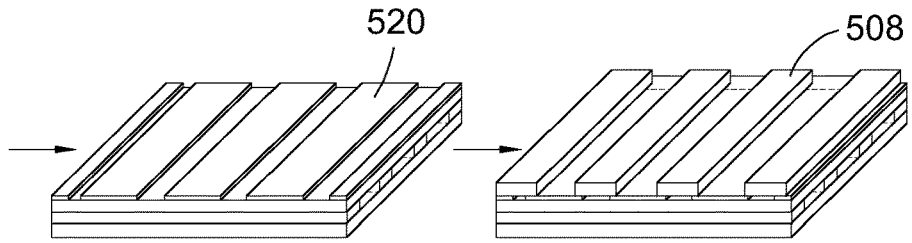
Figures 5G, 5H:
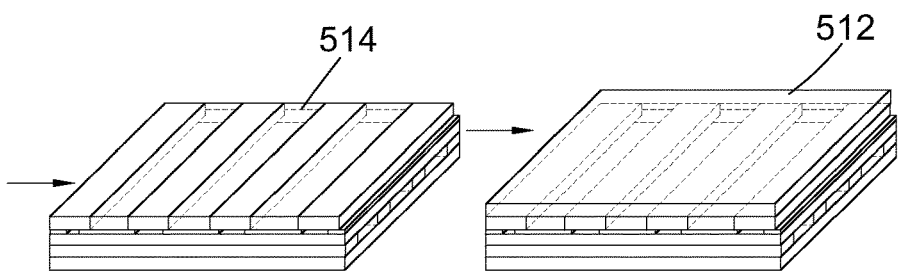
Figure 5I:
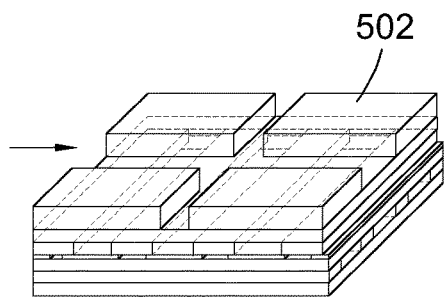

FIG. 5A to 5I illustrate the steps of a particular method 500 of fabricating a sensor according to an embodiment of the invention. In FIG. 5A a base layer 504 is spin-coated, deposited, cast, or spray-coated into a thin membrane forming a bottom polymer encapsulation layer. Ideally, the base layer 504 is made of an insulating polymer with desired elastic properties, such as PDMS or Parylene-C which may also form part of the binder material of the active layer. If spin-coating, this may be done on a silanized silicon wafer, so that the polymer does not get stuck and the device can be peeled off after production. In FIG. 5B a first electrode layer 506 is screen-printed, cast, sputter-coated, or spin-coated (e.g. using a photolithographic pattern) into a matrix array of bottom column electrodes. The first electrode layer 506 can be composed of conductive adhesives, such as carbon-impregnated elastomers, intrinsically conductive polymers, such as poly(3,4-ethylenedioxythiophene) polystyrene sulfonate (PEDOT:PSS) or a metal, such as gold or silver. FIG. 5C shows an optional step of adding an insulation layer 514 between each column electrode in the first electrode layer 506 for additional rigidity or robustness, using screen-printing or photolithographic patterning. In this case, the insulation layer 514 may be of the same material as the base layer 504. FIG. 5D shows the screen printing, casting, spin-coating, spray-coating or attachment of a thin active layer 510, for example, of a quantum tunnelling material such as those described above. The thickness of the active layer 510 may determine the sensitivity of the sensor and can vary from tens of microns to millimetres. The type of metal as well as the binding matrix material can vary according to the desired application and the composition of the material may be in the form of a liquid or solid. For example, the active layer 510 could include gold nanoparticles and PDMS, or alternatively could include magnetite and water based polymeric ink. It may be a known material or a custom formulated material. FIG. 5E shows the screen-printing, casting, sputter-coating, or spin-coating (e.g. using a photolithographic pattern) to create a thin layer (~10-100 um thick) of binder material to form spacers 520 only in areas between where electrodes are to be deposited, such that the electrode edges sit on top of the spacer edges. These spacers form a small air gap between the electrodes. Standard microfabrication or chemistry techniques such as patterning a layer which is partially dissolvable using e.g. photo-curable polymers may be utilised to create the air gap. FIG. 5F shows the screen-printing, casting, sputter-coating, spin-coating or attachment (e.g. using a photolithographic pattern) to form a matrix array of top electrodes in a second electrode layer 508, perpendicular to the first electrode layer 506, on top of the spacers 520. The second electrode layer 508 can be composed of conductive adhesives, such as carbon-impregnated elastomers, intrinsically conductive polymers, such as PEDOT:PSS or a metal, such as gold or silver. Optionally, a support layer is provided between the spacers 520 on which the top electrodes are formed. FIG. 5G shows an optional step of adding an insulation layer 514 between the top electrodes in the second electrode layer 508 for additional rigidity or robustness, using a screen-printing or photolithographic patterning technique. As above, the insulation layer 514 may be of the same material as the base layer 504. In FIG. 5H a top layer 512 is spin-coated, deposited, cast, or spray-coated into a thin membrane to form a top polymer encapsulation layer. The top layer 512 may be made of an insulating polymer with the desired elastic properties, such as PDMS or Parylene-C and ideally may be formed of the same material as the binder material of the active layer 510. In FIG. 5I four three-dimensional surface bumps 502 are added into the top layer 512 by casting a polymer layer to form bumps 502 over every set of four overlapping electrodes or sensels. Notably, the bumps 502 may have a different elasticity and rigidity to the rest of the sensor (e.g. the bumps 502 may be more rigid than the sensor body). The three-dimensional shape of each bump 502 may be a cube, cone, or mesa/hemisphere, for example, and its corners should overlap to some extent with the four underlying electrodes. This gives each group of 4 electrodes (i.e. sensels) in the array the ability to become a single three-dimensional or tri-axial force sensing tactile element (tactel). After every step described in the method 500, an optional oxygen plasma layer, thiol layer or other chemical adhesive layer may be added to increase robustness of the sensor. If the base layer 502 has been spin-coated, then a further step may be required to detach the entire assembly from a wafer by peeling it off.

If the binder material for the above method is a stretchable elastomer, then it is possible to also make the entire sensor array stretchable, further increasing its potential applications.

The substrate or base layer 504 used to create the sensor depends somewhat on the application. Traditional flexible electronics substrates that are complaint in only one axis such as PET (Polyethylene Terepthalate) varying in thickness from 25-125 microns and PEN (Polyethylene Naphtalate) varying in thickness from 10-100 micron (usually 25 micron) can be employed. These materials may be required when a high resolution is required, or in the case that the device needs to be resistant to a harsh external environment such as underwater. For less harsh conditions, substrates compliant in more than one axis such as TPU (Thermoplastic Polyurethane) or silicone can be used. Or TPU coated silicone in order to reduce shrinkage induced in silicone during thermal curing of nanocomposite inks after deposition. These materials may also be in the thickness range of between 25-125 microns. Non-woven fabrics may also be used as a substrate, as well as paper, and various rubbers or latex. A variety of other polymers can also be used as a substrate. Parylene-C can be used in a range of 10 nm-1 micron, for example, for biocompatible applications or ones that require extreme compliance and/or a complete seal to the outside world. Furthermore, an oil may be provided on top of the substrate, if necessary, in order to facilitate the spreading of ink for the electrodes during the printing process.

A first layer of conductive ink may be printed, which functions as the conductive tracks for the first electrode layer 506 and is highly conductive. In order to define the matrix pattern for this first electrode layer 506, a stencil film or mask or screen printing mesh with appropriate openings cut out or washed away with solvent may be used, through which the ink can be spread onto the substrate using a squeegee as is common in screen printing or roll-to-roll printing. Having a sheet resistivity in the range of 0.05 ohm/mm$^2$ this electrode layer is made of a nanocomposite material and may be either flexible of stretchable. Stretchable inks work with substrates that may allow a percentage of stretch, such as TPU or silicone. Such inks contain conductive particles with one dimension often in the order of nanometers and an overall size often in the order of microns, and which are embedded into a polymer matrix usually mixed with solvent chemicals and surfactants that ensure an even dispersion between the particles in the ink. The particles typically consist of silver or carbon, but can equally be composed of gold, graphene, copper, tungsten, zinc, etc. The thickness of the deposited ink may be of the order of 10-50 microns (sometimes 100) in screen printing, but can also be less if inkjet printing it used. The width of some electrodes can be as low as 20 micron up to 1 millimeter.

After the electrode ink is deposited, it must be cured, usually at a temperature between 80-120° C. During the curing process, part of the solvent evaporates while curing the polymer composite material.

The composition of tracks which may be required to connect the sensor to readout electronics and the electrodes themselves may either be the same composition, or made from a different composition. Optionally, a coating with an ink with a different composition may be printed for the electrodes, on top of conductive tracks that extend to a region underneath each electrode.

One or more layers of sensitive (potentially anisotropic i.e. being only sensitive to the normal direction, by means of the material thickness or its intrinsic properties) active layers is provided in each sensor.

In addition, spacers consisting of a dielectric polymer may be printed or deposited onto the sensor using droplet dispensing methods. These spacers, which may be ~10-50 microns in height, and 1-200 microns in diameter or width, act to keep the grid layers of the sensor separated from each other until a specific force is applied. They also act to redistributed the force and prevent creasing or wrinkling of the sensor skin when bent, which in turn could create local pressure points or 'bubbles' that could cause a pressure reading on the sensor.

Once the sensors are printed, stiffeners may be added to the ends of the connected electrode traces or tracks in the case of a highly compliant and stretchable material, or one that is extremely thin such as 25 micron or less, so that normal solder tabs or cables can be crimped to them, and the sensor electronics can be connected to a rigid electronic processing circuitry.

Figures 6A, 6B:
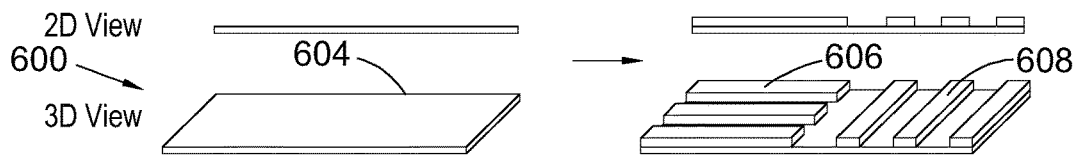
FIG. 6A to 6I illustrate the steps of a method of fabricating a sensor according to a further embodiment of the invention.
Figures 6C, 6D:
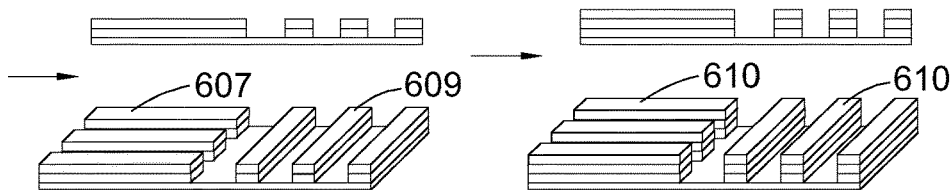
Figures 6E, 6F:
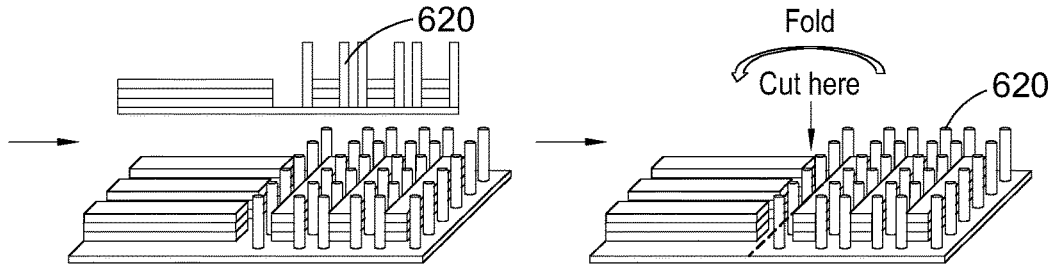

FIG. 6A to 6I illustrate the steps of a method 600 of fabricating another sensor according to a further embodiment of the invention. In each step, the sensor is shown in both a three-dimensional and two-dimensional view. In FIG. 6A, an appropriate substrate material 604 (e.g. PEN, PET, TPU, PDMS, TPU coated Silicone, Latex, etc.) is chosen and is fabricated to a desired thickness. In this case, the substrate 604 will form both a base layer and a top layer of the sensor as will be described in more detail below. In this embodiment, the substrate 604 is PET which is 36 microns in thickness. FIG. 6B shows a step of printing (e.g. screen-printing or inkjet printing) both a first electrode layer 206 and a second electrode layer 608 in a matrix array with row and column electrodes oriented perpendicularly to one another. The electrodes are formed from an ink typically containing silver or low resistance carbon. In this embodiment, the electrodes are made from CI-1036 stretchable silver-based conductive ink with low sheet resistivity of <0.010 Ω/square at 25.4 microns thickness. In this example, the electrodes are screen printed at an emulsion thickness and hence have a thickness before curing of 14 to 25 microns. Each electrode has a width of 2 mm and three electrodes are provided in each of the first and second electrodes layers 606, 608 so as to form a sensor which will be 1 cm wide by 1 cm long when assembled. A gap of 2 mm is provided between the first electrode layer 606 and the second electrode layer 608 on the substrate 604 to allow each layer to be easily separated as will be described below. FIG. 6C shows an optional step of screen printing a carbon layer 607, 609 on each of the electrodes in the first and second electrode layers 606, 608. FIG. 6D shows a step of depositing (e.g. screen printing, inkjet printing, electro-spinning) an active layer 610 on each of the electrodes in the first and second electrode layer 606, 608. The active layer may comprise a piezoresistive and/or quantum tunnelling and/or piezoelectric material layer and can be deposited as a single layer or multiple layers on top of one another so as to control the layer thickness. The active layer may comprise a continuous sheet or discrete portions, for example, in the form of lines, squares, dots or other shapes. In this embodiment, the active layer is formed of Quantum Technology SuperSensors (QTSS®) C75 piezoresistive ink printed on top of the electrode columns and rows on only the grid regions and with a similar thickness as the previous layers. In FIG. 6E a spacer layer 620 is deposited using dielectric, insulating or conductive material. The spacer layer 620 may be deposited, for example, by screen printing, inkjet printing or using droplet dispenser. In this embodiment, the spacer layer 620 is formed on only one side of the substrate 604 in the gaps between the electrodes forming the second set of electrodes 608. In this example, the spacer layer 620 comprises an array of cylindrical posts, each having a diameter of 50 microns and a height of 100 microns, and being provided at a spacing of 1 mm across the substrate 604. The material used for the spacer layer 620 in this example is a dielectric such as EMS DI-7548 which is stretchable as well as flexible. The spacer layer 620 can be printed on one side of the sensor in a single thick layer, multiple layers on top of one another, or both sides of the sensor if the layers are thin (although this requires precision alignment).

Figures 6G, 6H:
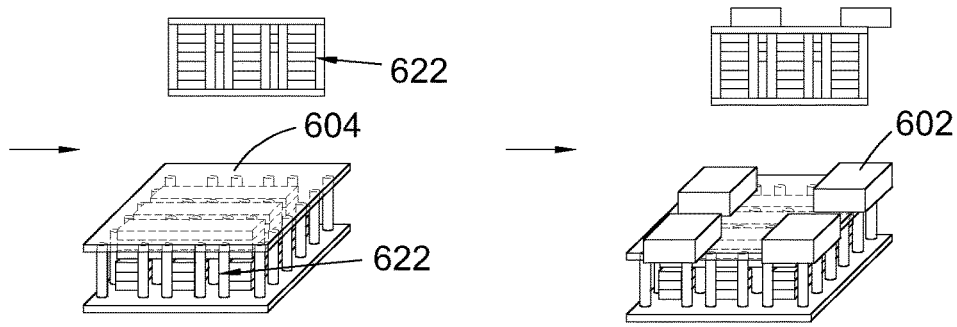

In FIG. 6F, the substrate 604 is cut, for example, with scissors, a laser, a knife plotter or scalpel to separate the first electrode layer 606 and the second electrode layer 608 into two parts. The two parts are then folded inwardly such that the second electrode layer 608 is stacked above the first electrode layer 606 to form a conductive matrix grid as shown in FIG. 6G. In this configuration the substrate 604 attached to the second electrode layer 608 forms the top layer of the sensor. In addition, the posts of the spacer layer 620 extend between the substrate 604 forming the base layer and the substrate 604 forming the top layer such that there is an air gap 622 between the active layer 610 portions provided on the first electrode layer 606 and the second electrode layer 608. When the sensor is stacked like in FIG. 6G, the spacer layer 620 serves to distribute force when the sensor is bent, and in this case also serves to maintain the air gap between the active layers 610, making sure an open circuit is present until a given offset force is applied. In some embodiments, the sides of the sensor may be bonded with an adhesive paste (e.g. silicone PDMS) applied along the edges of the device and around the sensing layers region so as to seal it from the outside environment and laminate for sides of the sensor to each other in a durable manner. In addition, a vapour deposit of APTES (3-aminopropyl triethoxysilane) linker may be applied onto the top layer for 1 h. In some embodiments, the sensor may be fully coated with a compliant polymer such as latex at this stage. For extremely thin sensors, a dip-coating technique may be used.

As shown in FIG. 6H, bumps 602 are then applied to the top surface of the sensor for translating fore into torque. In order to sense both the direction as well as the magnitude of the force, the bumps should be placed in the centre of each set of 4 orthogonally arranged electrodes (sensels), which converts any force applied into a torque when pressed. The torque will then compress some of the sensels more than others, and this can be read-out through an attached electronic circuit. The bumps can be made by printing multiple dielectric layers using various printing techniques (including 3D printing or silicon etching), or by casting the bumps in a mould (in this case the sensor needs to be placed upside down on the mould while the polymer to be used is in liquid state or partially cured state, then the entire assembly must be cured. In this embodiment, a master mould is made from PLA for the four cubic bumps 602 which are 2 mm in height and 6 mm in length and width. Liquid PDMS (or silicone/latex/TPU/Rubber) is then cast into the mould (with a 10:1 weight ratio of elastomer to curing agent) and cured in an oven for 1 h at 80 degrees Celsius. After this, the PDMS is treated with UV-Ozone or oxygen plasma to further increased adhesion before it is bonded to the PET top layer of the substrate 604. The assembly may be left to sit overnight to enable strong bonds to form between the PDMS bumps and the PET. The bumps 602 may be rigid or compliant themselves, as long as they allow the device to flex at the given thickness. Thinner bumps 602 as well as those made from highly compliant materials will distort measurements less upon bending and thus give better anisotropic selectivity to normal forces while the device is in a bent state.

Figure 6I:
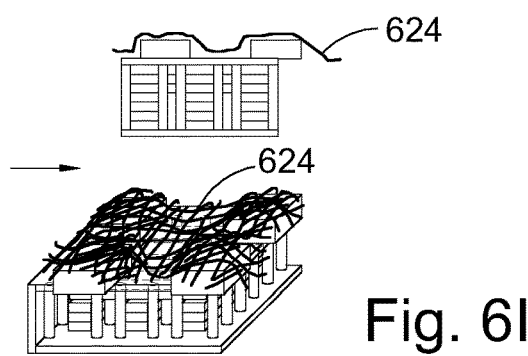

As shown in FIG. 6I, a final optional step may comprise laminating or insulating a top of the sensor or edges of the sensor or the entire sensor structure to make a cover layer 624 which is impermeable to outside elements. Lamination can be done with e.g. a Parylene coating which is completely conformal (more specifically Parylene-C of 1 nanometer to 1 micron thickness), and insulation may be achieved with a silicone, rubber, polyurethane, or other polymer blend.

It will be understood that any suitable printer can be employed for any of the layers in the sensor. However, an example of a suitable screen printer is Horizon Dek i3™.

The readout of the sensor can be done using a known zero potential method. This minimizes crosstalk between adjacent sensors within large arrays. In resistive array circuits, a large interference current can be generated when the resistance of one sensing element approaches that of others around it. In a negative piezoresistive coefficient sensor such as the ones described here, the sensing elements begin at a high resistance and reduce in resistance as pressure is applied. This means that in the sensors described, low pressures produce a higher interference as the material has a high resistance at rest. Moe details on the operation of these sensors are provided below in relation to FIGS. 12A to C.

FIG. 7A to 7G illustrate the steps of a method of fabricating a sensor according to a yet further embodiment of the invention. This sensor can be considered a 4-wire single point sensor which operates differently to the other sensors described above. In particular, this sensor differs in that it measures the 'centre of mass' of the pressure being applied in a resistive area that is between the 4 wires in the electrode grid. The bump for this sensor functions in a similar way to a joystick in that the position of the centre of mass can give us the direction of force.

Figure 7A:
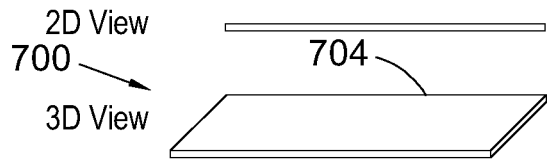
FIG. 7A to 7G illustrate the steps of a method of fabricating a sensor according to a yet further embodiment of the invention.
Figure 7B:
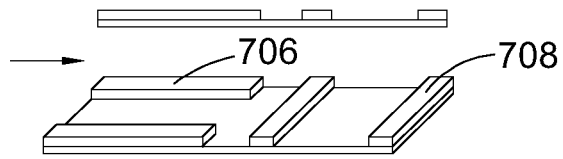

As shown in FIG. 7A an appropriate substrate 704 material is selected along with its thickness. In this embodiment, the substrate 704 is formed of PET at 36 microns thickness. FIG. 7B shows the screen printing of both the first and second electrode layers 706, 708 on the same substrate 704, with the electrodes in each layer oriented perpendicularly to each other. In this embodiment, the electrodes are made of EMS CI-1036™ stretchable silver-based conductive ink with a low sheet resistivity of <0.010 Ω/square at 25.4 microns thickness. In this embodiment, the electrodes are screen printed at an emulsion thickness such that the ink thickness before curing is 14 to 25 microns. The electrodes are 2 mm wide and only two electrodes are provided along the edges of each of the first and second electrode layers 706, 708 to form a 1 cm by 1 cm footprint sensor.

Figure 7C:
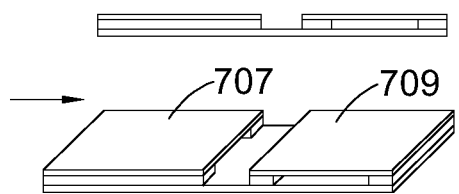

FIG. 7C shows the screen printing of a first high resistance carbon layer 707 deposited on top of and extending between the two electrodes in the first electrode layer 706 and a second high resistance carbon layer 709 deposited on top of and extending between the two electrodes in the second electrode layer 709. In this embodiment, both high resistance carbon layers are blended from two Henkel™ inks called ECI 7004 HR and NCI 7002 Ink (80/20% by weight blend) to give a sheet resistivity of ~10,100 Ω/square/mil at 10 microns thickness after curing. The deposition is performed through a mesh with ~20-40 microns emulsion thickness. In other embodiments, the high resistance carbon layers may be formed using EMS™ CI-2050 LR (1,500-2,500 Ω/square/mil at 25.4 microns) and/or HR (>10M Ω/square/mil at 25.4 microns). In some embodiments, the first and second high resistance carbon layers 707, 709 may be different.

For this type of sensor it is important that the high resistance carbon layers 707, 709 are of a much higher resistance than the sum of the lead resistance within the device and the contact resistance for interfacing with the outside world. The reason for this is that, when a voltage is applied across the top electrode layer 708 or the bottom electrode layer 706 of the device, it is desirable that most of the voltage drop occurs within the resistive carbon region. This ensures that the position of the centre of pressure of the torque applied to the bump layer may be measured: when a pressure is applied to the device, both active layers 710 contact each other around a given point. If a potential difference is applied across the electrodes on one side (top or bottom) of the device, and a voltage measured from either of the electrodes on the other side of the device, this forms a potential divider circuit. The voltage read out from one of the electrodes opposite to the carbon plane which has a potential difference being applied across it will give the location of pressure (in one axis) between the two electrodes where the pressure is being applied. This electrical configuration can be flipped in order to readout the position of the other axis with the electrodes/carbon layer on the opposite side of the device.

Figure 7D:
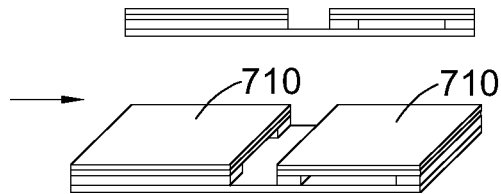

FIG. 7D shows the screen-printing, inkjet printing or electro-spinning of an active layer 710 on each of the first high resistance carbon layer 707 and the second high resistance carbon layer 709. In this embodiment, the active layer 710 is formed of Quantum Technology SuperSensors (QTSS®) C75 piezoresistive water-based ink.

Figure 7E:
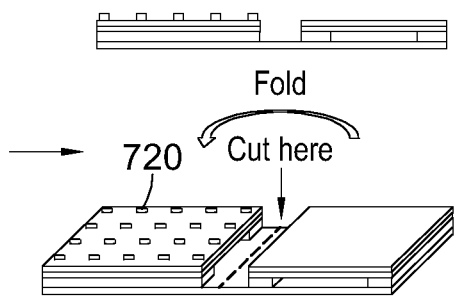
Figure 7F:
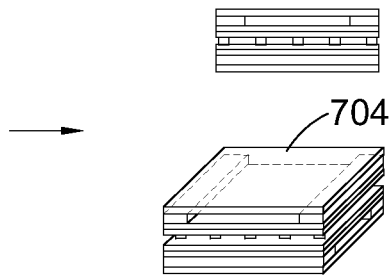

In FIG. 7E a spacer layer 720 comprising a square array of short cylindrical spacer dots is provided on the active layer 710 on one side (the first side) of the substrate. Each spacer dot is 200 microns in height and is spaced 2 mm apart from its neighbour. In this embodiment, the spacer layer 720 is printed using Stratasys' Tango™ (i.e. TangoPlus™, FLX930) material, which is a PolyJet™ printable material that simulates rubbery thermoplastic elastomers. The typical properties of the material are a shore hardness of 26-28 and an elongation at break at 170-220%. The spacers can therefore withstand the difference between tensile and compressive stress at the top and bottom of the device while curved, even if applied while the device itself is flat. The substrate 704 is then cut, for example, with scissors, a laser, a knife plotter or scalpel to separate the first electrode layer 706 and the second electrode layer 708 into two parts. The two parts are then folded inwardly such that the second electrode layer 708 is stacked above the first electrode layer 706 to form a conductive matrix grid as shown in FIG. 7E. In this configuration the substrate 704 attached to the second electrode layer 708 forms the top layer of the sensor. In addition, the posts of the spacer layer 720 extend between the active layer 710 on the first electrode layer 706 and the active layer 710 on the second electrode layer 708 such that there is an air gap in the middle of the active layer 710 as shown in FIG. 7F. Once the device is cut and folded, the sides are bonded with a silicone PDMS adhesive applied around the edges of the device. A vapour deposit of APTES (3-aminopropyl triethoxysilane) linker is then applied onto the top surface of the device for 1 h in order to facilitate PDMS adhesion described below.

Figure 7G:
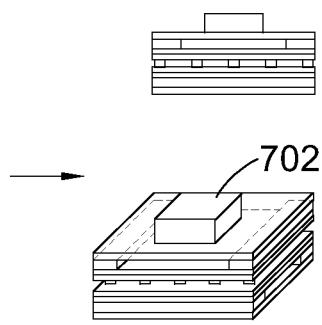

In FIG. 7G, a bump 702 is provided in the middle of the sensor, spaced from the electrode grid. The bump 702 may be cast or printed and many polymers can be used for this, e.g. more compliant PDMS, or less compliant SU8. The bump 702 can have various shapes, sizes, and heights depending on the desired application. In this embodiment, a master mould is made from PLA for the cuboid bump 702 which is 2 mm in height and has a length and width of 6 mm. Liquid PDMS is cast into the mould (10:1 weight ratio of elastomer to curing agent) and cured in an oven for 1 h at 80 degrees Celsius. After this, the PDMS is treated with UV-Ozone or oxygen plasma to further increased adhesion before it is bonded to the top layer of the substrate 704. The assembly is left to sit overnight to enable strong bonds to form between the PDMS bumps and the substrate 704.

For this type of sensor, the readout consists of three separate readings for each bump 702. One reading is required for the X-location and another for the Y-location as explained below. Each time, a voltage (and current) is applied across the electrodes of one plane (i.e. the first or second electrode layer 706, 708) and one of the electrodes on the opposite plane (i.e. the other of the first or second electrode layer 706, 708) is used to readout a voltage. This forms a potential divider circuit where the voltage being read corresponds to the (x or y) position at which both planes touch, which is where the force is being applied. It is important that the high resistance carbon layers are much higher in resistance that the leads and contact resistances connecting the device to the outside world, so that they are essentially negligible. Otherwise, the location readings become restricted as some significant voltage drop will occur in the leads.

For reading out the force itself, a current must be passed from one plane to the other, with the active layer 710 (i.e. piezoresistive material) in between. This can be done by applying a potential difference between one electrode on the top plane (i.e. the second electrode layer 708) and another on the bottom plane (i.e. the first electrode layer 706). In this case, the pressure applied affects the active layer's resistance which in turn changes the current through the device. As a result of this, there is also a change in the overall voltage drop across the active layer 710. By using the opposing electrodes on both planes (which are not being used to transmit current), the voltage at either place can be measured. This corresponds to what is known as a 4-point probe measurement in electronics literature, since it does not measure the contact resistance or in this case the voltage drop in the electrodes to the device as well as their corresponding leads. However, since we are measuring voltage drop it is not perfect. Depending on the location of the pressure being applied, a different distance on the high resistance plane will need to be traversed by the current which leads to variable resistances and hence variable voltage drops in the resistive layers due to the location of the pressure being applied. Knowing the resistance of the high resistance layer as well as the uniformity informs how much the resistance measurements should be adjusted by based on the location, and by calibration of the device. Thus, when the bump 702 on top of the sensor experiences a force, its shear component causes a torque on the bump 702 which focuses the centre of the pressure into a particular region of the device. Measuring the location and magnitude of this allows measurement of the average direction and magnitude of the force.

Figure 8A:
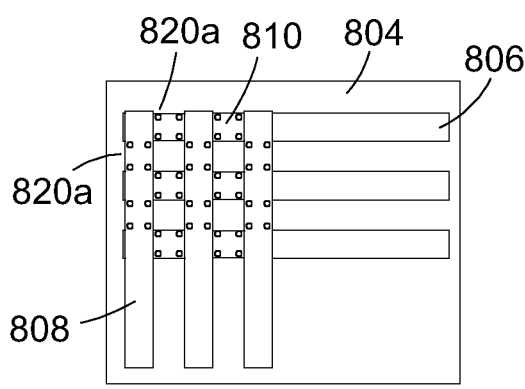
FIGS. 8A and 8B show plan views of a portion of a sensor including different cylindrical support post arrangements according to embodiments of the invention.

The spacers in any of the embodiments of the invention serve to distribute force and prevent wrinkles from forming in the sensor which would be registered falsely as pressure, while making sure an open circuit is present when no offset force is applied. FIGS. 8A to 110 show various example spacer arrangements for use in embodiments of the invention. For illustrative purposes only a portion of the sensor is shown in each case.

Figure 8B:
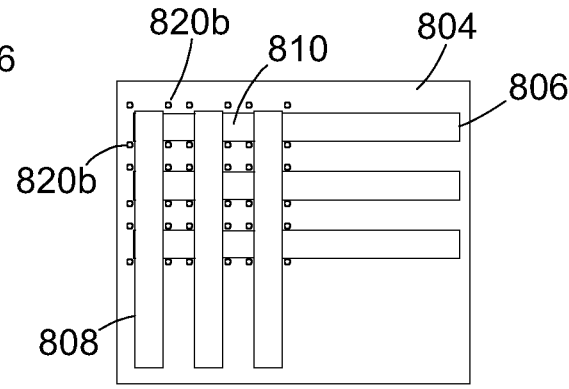

FIGS. 8A and 8B show plan views of a portion of a sensor including different cylindrical spacer arrangements according to embodiments of the invention. In both cases a substrate 804 is provided with three horizontal electrodes in a first electrode layer 806 and three orthogonal electrodes in a second electrode layer 808. An active material 810 is provided between the electrodes in the first electrode layer 806 and the second electrode layer 808. In both cases, the spacers are formed of cylindrical posts, pillars or dots.

In FIG. 8A the spacers 820a are printed on both sides of the substrate 804, and are arranged to extend from or through each electrode layer to the substrate 804 between electrode matrix overlaps.

In FIG. 8B the spacers 820b are printed on only one side of the substrate 804, and are arranged to extend between the lower and upper portions of the substrate 804 between electrode matrix overlaps.

The spacers in FIGS. 8A and 8B may be formed of polymers such as dielectric polymers, polysiloxanes, rubbers or silicones or amorphous crystalline substances such as glass. The spacers may be shaped to be cylindrical, cone or cone section, pyramid or pyramid section, cuboid, hemispherical or hemispherical section, half-cylinder, tetrahedron or tetrahedron section, hexahedron, triangular prism, polyhedron, other shapes. In some embodiments, the spacers may be graded such that they change in height, shape, dimensions or spacing across the sensor. In an example, the spacers may be cone shaped with a width of 50 microns, a height of 25 microns and a spacing of 1 mm.

Figure 9A:
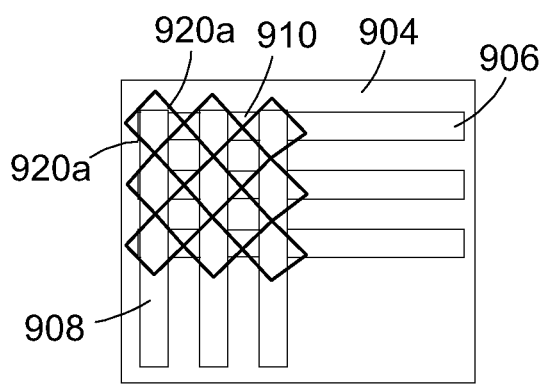
FIGS. 9A and 9B show plan views of a portion of a sensor including different diamond support post arrangements according to embodiments of the invention.
Figure 9B:
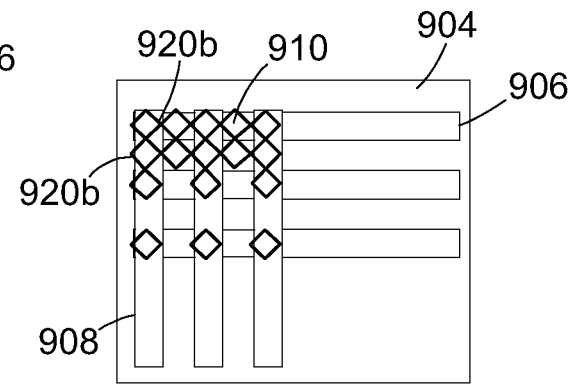

FIGS. 9A and 9B show plan views of a portion of a sensor including different diamond spacer arrangements according to embodiments of the invention. In both cases a substrate 904 is provided with three horizontal electrodes in a first electrode layer 906 and three orthogonal electrodes in a second electrode layer 908. An active material 910 is provided between the electrodes in the first electrode layer 906 and the second electrode layer 908. In both cases, the spacers are formed of a diamond or square mesh.

In FIG. 9A the spacers 920a are printed on only one side of the substrate 904, and are arranged to extend from or through each electrode layer between electrode matrix overlaps.

In FIG. 9B the spacers 920b are printed on both sides of the substrate 904, and are arranged to extend on and/or between the lower and upper portions of the substrate 904 on and/or between electrode matrix overlaps.

The spacers in FIGS. 9A and 9B may be formed of a woven fabric mesh or flexible/rubbery polymer mesh which is, for example, 3D printed using any of various soft polymers.

Figure 10A:
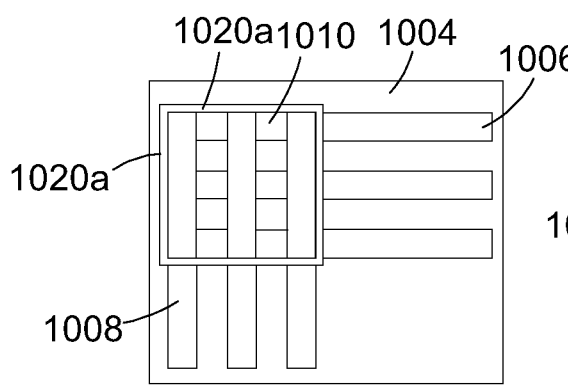
FIGS. 10A and 10B show plan views of a portion of a sensor including different square support post arrangements according to embodiments of the invention.
Figure 10B:
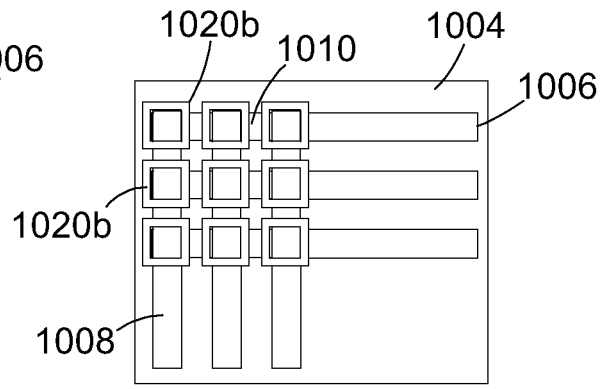

FIGS. 10A and 10B show plan views of a portion of a sensor including different square spacer arrangements according to embodiments of the invention. In both cases a substrate 1004 is provided with three horizontal electrodes in a first electrode layer 1006 and three orthogonal electrodes in a second electrode layer 1008. An active material 1010 is provided between the electrodes in the first electrode layer 1006 and the second electrode layer 1008. In both cases, the spacers are formed of a hollow square post.

In FIG. 10A the spacers 1020a are printed on only one side of the substrate 1004, and are arranged to extend around a large sensor area, for example, encompassing nine electrode overlaps with a single square.

In FIG. 10B the spacers 1020b are printed on only one side of the substrate 1004, and are arranged to extend around a small sensor area, for example, between each electrode matrix overlap.

The spacers in FIGS. 10A and 10B may be formed of similar materials to those described above for the cylindrical or diamond spacers.

Figure 11A:
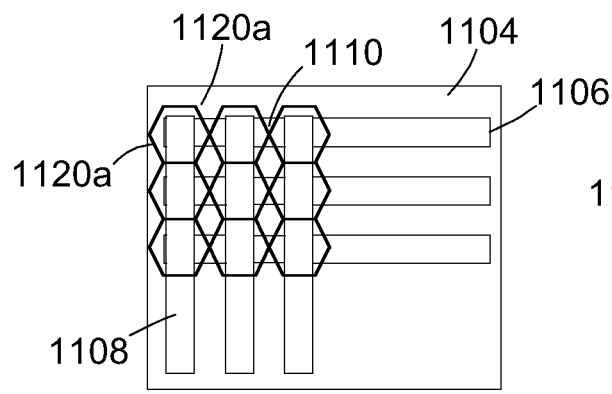
FIGS. 11A, 11B and 11C show plan views of a portion of a sensor including different hexagonal support post arrangements according to embodiments of the invention.
Figure 11B:
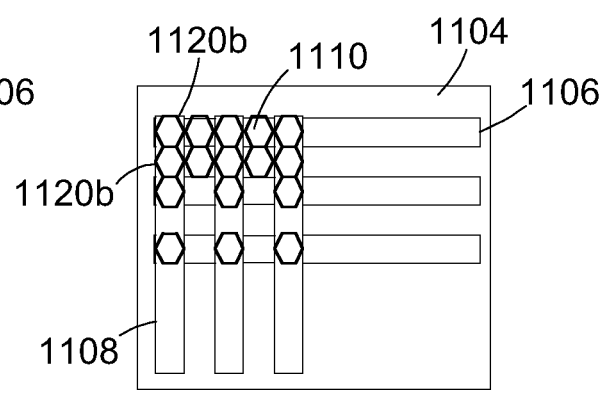
Figure 11C:
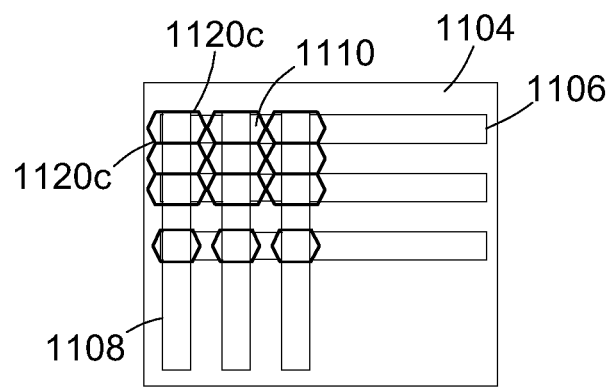

FIGS. 11A, 11B and 11C show plan views of a portion of a sensor including different hexagonal spacer arrangements according to embodiments of the invention. In each case a substrate 1104 is provided with three horizontal electrodes in a first electrode layer 1106 and three orthogonal electrodes in a second electrode layer 1108. An active material 1110 is provided between the electrodes in the first electrode layer 1106 and the second electrode layer 1108. In each case, the spacers are formed of a hollow hexagonal (i.e. honeycomb) mesh of a different size.

In FIG. 11A the spacers 1120a are printed on only one side of the substrate 1104, and are arranged to extend between electrode matrix overlaps.

In FIG. 11B the spacers 1120b are printed on only one side of the substrate 1104, and are arranged to extend around a small sensor area, on and/or between each electrode matrix overlap.

In FIG. 11C the spacers 1120c are printed on only one side of the substrate 1104, and are arranged to extend between electrode matrix overlaps and to bound said electrode matrix overlaps.

The spacers in FIGS. 11A, 11B and 110 may be formed of extruded or printed meshes. These may be in the shape of honeycomb, triangular, quadrilateral, diamond, diamond with ferrule, square or plain. A variety of different weaves can be chosen depending on the application and must ensure enough of the sensors active layers can contact one-another. The woven mesh has the same purpose as other spacer layers. A plain Dutch weave, twill weave, plain weave, twill Dutch, lock crimp, inter-crimp, twill Dutch double or stranded weave may be employed amongst others. The mesh may be made of non-conductive textile thread or electrically conductive thread (e.g. silver or titanium) could be used for enhancing sensitivity while distributing pressure within the sensor.

In order to make a fully compliant sensor which is flat, there are multiple challenges: the sensor must be thin, electrodes must be compliant, and the sensor must not react to forces other than the one desired. A quantum tunnelling active layer material is advantageous as it starts at a very high resistance (~$10^9 \Omega$). Contacts to this material can be made up of multiple different materials, however the electrodes must be compliant and slightly elastic so that the material can be used to wrap around objects. One way to do this is to make stretchable silver electrodes, or alternately use conductive adhesives, even if they vary slightly according to pressure.

As explained above, it is possible to make a grid/matrix of these sensors by sandwiching the active layer between row and column electrodes travelling in perpendicular directions on either side. This has previously been done with non-compliant electrodes and electronics, and even with 'flexible' electronics which have a limited bending radius but are not fully compliant over any macroscopically observable surface. In order to readout a matrix, a multiplexer is required which reads out every sensel (sensing pixel) in the array one by one, and is attached to a microcontroller or other signal processing hardware and software.

In embodiments of the invention, a simple device is proposed, where not only is the entire device itself compliant, but every cluster of 4 sensels in a grid can be transformed into a 3D force sensing 'tactel' (tactile pixel) by including 'bumps' or shapes which act as a force transmission structure for the top layer of the device.

The device proposed is made for mass-production using printing such as roll-to-roll printing, screen printing or similar microfabrication techniques.

The main working mechanism of the sensors described above is the following: changes in the resistance of each of the 4 sensels, as well as their normal distribution, are used to estimate tri-directional forces on the sensor. Each bump acts as a force transmission structure. By applying a directional force onto each bump, a stress is generated by deforming the 'bump'. The normal component of the force compresses each sensel underneath it equally (resulting in symmetrical resistive changes), however the shear component generates a torque in the active layer which compresses some sensels more than others (resulting in an asymmetrical resistance change). Tuning the sensitivity of this can be done both by varying the thickness and binding material of the active layer as well as the height and rigidity of the 'bump' and the underlying substrate materials.

Individual grid lines can be made as small as 10 um, and the spacing between then as small as necessary provided tunnelling is not established between the layers which would create cross-talk and short-circuits.

In order to read-out the signal, each column and row electrode must be connected to appropriate electrical readout circuitry. When reading out the signal, since each electrode is spatially separated from one another, resistive cross-talk noise is significantly reduced. However, to achieve a further reduction in cross-talk or an increase in the signal-to-noise ratio (SNR) of each sensel, one of the following methods may be adopted: i) Pubrick's voltage mirror method, where drive lines that are not under consideration at a measuring point are set at a potential equal to the output voltage, or ii) the simpler zero potential method where the voltage of the scanning electrodes is set to zero. These form an equal potential zone that eliminates the effect of cross-talk. There are multiple ways to configure the above circuits in practice.

Calibration of the device is necessary, however a machine learning or artificial intelligence algorithm may also be able to 'learn' how the sensor works if it given appropriate training data. The force ranges that can be measured with such a sensor range from 0.01N up to a theoretically infinite quantity, depending on the formulation of the active layer, its binder, and the overall thickness of the sensor.

None of the layers have a preferred thickness, however for the entire device to be compliant it is expected that they be no more than 1 mm thick and no less than 10 nm thin. The bumps on the surface may comprise different shapes to those listed, however the constraint of having 1 bump for every 4 sensels applies in most cases.

Figure 12A:
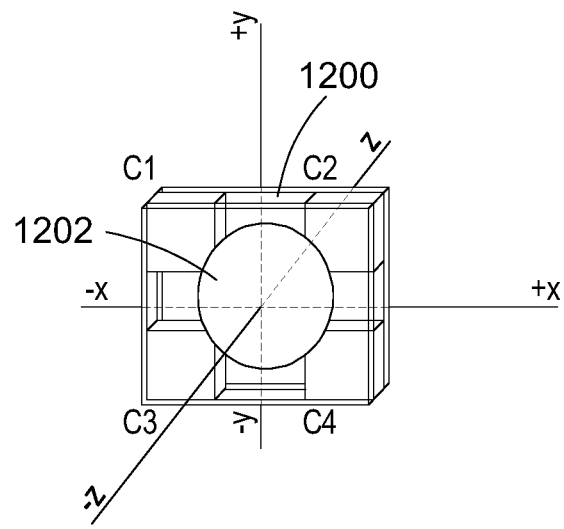
FIG. 12A shows a top perspective view of a single tactile element (tactel) of a sensor according to an embodiment of the invention.

FIG. 12A shows a top perspective view of a single tactile element (tactel) 1200 of a sensor according to an embodiment of the invention. This tactel has a dome-shaped bump 1202 provided over 4 sensels C1, C2, C3 and C4 which represent the pixels to be read. Table 1 below shows the change in electrical resistance experienced by each of the 4 sensels when subjected to different forces. Thus it can be determined how the electrical readout for such a sensor can be translated into a measurement of the position, size and direction of an applied force.

TABLE 1

Sensel change in response to force direction

| | | Change of electrical resistance | | | |
|---|---|---|---|---|---|
| Direction of force | | C1 | C2 | C3 | C4 |
| Shear force | +X | | + | | + |
| | −X | + | | + | |
| | +Y | + | + | | |
| | −Y | | | + | + |
| Normal force | Z | + | + | + | + |

Figure 12B:
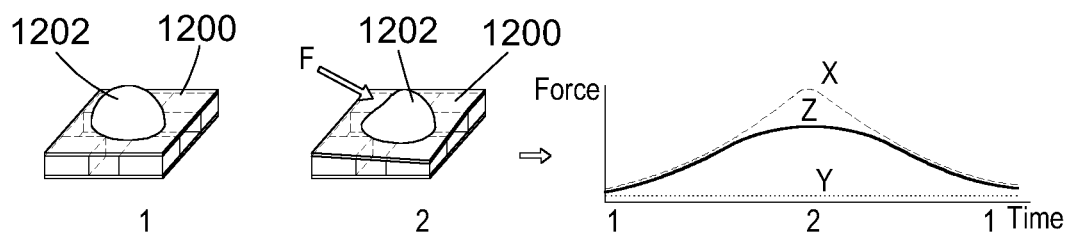
FIG. 12B shows a side perspective view of the tactile element of FIG. 12A before and after an oblique force is applied along with a corresponding force v time graph.

FIG. 12B shows a side perspective view of the tactile element 1200 of FIG. 12A before and after an oblique force is applied to the bump 1202, along with a corresponding force v time graph. This illustrates the difference in force experienced in the x, y and z axes when the oblique force is applied.

Figure 12C:
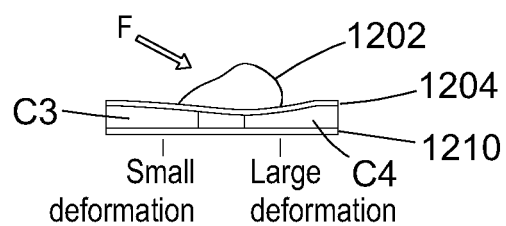
FIG. 12C shows a side view of the tactile element of FIG. 12B when the oblique force is applied.

FIG. 12C shows a side view of the tactile element 1200 of FIG. 12B when the oblique force is applied to the bump 1202. This shows a simplified sensor layer structure for ease of illustration which comprises an active layer 1210 sandwiched between an upper and lower substrate 1204. In this example, the sensel C3 experiences a small deformation while the sensel C4 experiences a large deformation on application of the force. This is translated into a weaker change in C3 than in C4 which helps to pinpoint the direction of the applied force.

There are multiple applications for the sensors described. These stem from large industrial, domestic, and healthcare demand for compliant tri-axial force sensors that work reliably. Examples include robotics (hard and soft robots, slip detection), electronic skin, prosthetics, human-robot-interaction, haptic systems and surfaces such as walls and floor, virtual reality, gaming, structural integrity monitoring (airplane wings, buildings), smart clothing (e.g. gloves), gait analysis insoles (ground reaction force direction, overall pressure, diabetic foot ulcer monitoring, etc. which can replace force sensing plates) sports impact monitoring (which can detect direction and magnitude of impact), implantable devices, wearables (e.g. for smart home use), biomedical devices, drug delivery patches/systems, stretchable electronic circuits, adult and sex toy industry (e.g. toys or dolls with real-time performance/feedback and/or adaptive devices), pillows that sense movement, hospital beds that monitor bed sores, blood pressure monitoring and detection (e.g. for coronary heart disease (CVD) diagnosis by monitoring blood pressure and flow through e.g. a garment or wearable), muscular force/exertion, fatigue monitoring and detection, tidal or wind turbine monitoring of flow characteristics around a blade to increase lifespan or energy generation capacity, all areas where autonomous robots may be envisaged and require high levels of dexterity and tactile information (e.g. warehouse picking and sorting, space exploration, search and rescue, elderly care, cooking, electronics assembly, fish-catching, social robots, etc.), aeroplane wings (monitoring loads/forces which can help in weight and cost reduction as well as better wing design), monitoring of forces in construction work environments, horse saddle pressure monitoring, muscular force mapping/monitoring, tissue hardness/density monitoring (e.g. diagnosis of breast cancer/how close a woman is to giving birth), prosthetics (e.g. for amputees but also for tremor compensation for certain diseases such as Parkinson's, ALS, etc.), amongst others.

In some embodiments, piezoresistive and piezoelectric layers could be stacked before applying a bump layer, in order to better imitate high and low frequency mechanoreceptors in the skin.

Furthermore, the device could be used upside-down (i.e. with the bumps abutting a user's skin and a force being applied through the base layer), which may be especially beneficial if aerodynamic or hydrodynamic properties are to be maintained on the surface of the device.

Whilst the foregoing description has described exemplary embodiments, it will be understood by those skilled in the art that many variations of the embodiments can be made within the scope of the present invention as defined by the claims. Moreover, features of one or more embodiments may be mixed and matched with features of one or more other embodiments.

REFERENCES

[1] U. Kim, D. H. Lee, Y. B. Kim, D. Y. Seok, and H. R. Choi, "A novel six-axis force/torque sensor for robotic applications," *IEEE/ASME Trans. Mechatronics*, vol. 22, no. 3, pp. 1381-1391, 2017.

[2] Y. Guo, J. Kong, H. Liu, H. Xiong, G. Li, and L. Qin, "Sensors and Actuators A: Physical A three-axis force fingertip sensor based on fiber Bragg grating," *Sensors Actuators A. Phys.*, vol. 249, pp. 141-148, 2016.

[3] S. Harada, K. Kanao, Y. Yamamoto, T. Arie, S. Akita, and K. Takei, "Fully printed flexible fingerprint-like three-Axis tactile and slip force and temperature sensors for artificial skin," *ACS Nano*, vol. 8, no. 12, pp. 12851-12857, 2014.

[4] S. Sundaram, P. Kellnhofer, Y. Li, J.-Y. Zhu, A. Torralba, and W. Matusik, "Learning the signatures of the human grasp using a scalable tactile glove," *Nature*, vol. 569, no. 7758, pp. 698-702, 2019.

[5] D. M. Vogt, Y. L. Park, and R. J. Wood, "Design and characterization of a soft multi-axis force sensor using embedded microfluidic channels," *IEEE Sens. J.*, vol. 13, no. 10, pp. 4056-4064, 2013.

[6] R. Agarwal and S. Bergbreiter, "Measurement of shear forces during gripping tasks with a low-cost tactile sensing system," 2019 2 nd *IEEE Int. Conf. Soft Robot.*, pp. 330-336, 2019.

[7] H. K. Lee, J. Chung, S. II Chang, and E. Yoon, "Real-time measurement of the three-axis contact force distribution using a flexible capacitive polymer tactile sensor," *J. Micromechanics Microengineering*, vol. 21, no. 3, 2011.

[8] K. Noda, K. Matsumoto, and I. Shimoyama, "Stretchable tri-axis force sensor using conductive liquid," *Sensors Actuators, A Phys.*, vol. 215, pp. 123-129, 2014.

[9] P. Yu, W. Liu, C. Gu, X. Cheng, and X. Fu, "Flexible piezoelectric tactile sensor array for dynamic three-axis force measurement," *Sensors (Switzerland)*, vol. 16, no. 6, 2016.

[10] Xiaoliang Chen, Jinyou Shao, Hongmiao Tian, Xiangming Li, Yazhou Tian, and Chao Wang, "Flexible three-axial tactile sensors with microstructure-enhanced piezoelectric effect and specially-arranged piezoelectric arrays," *Smart Mater. Struct.*, vol. 27, no. 2, p. 025018 (11 pp.), 2018.

[11] C. Hu, M. Q. H. Meng, M. Mandal, and X. Wang, "3-Axis magnetic sensor array system for tracking magnet's position and orientation," *Proc. World Congr. Intell. Control Autom.*, vol. 2, pp. 5304-5308, 2006.

[12] H. Wang et al., "A Low-cost Soft Tactile Sensing Array Using 3D Hall Sensors," *Procedia Eng.*, vol. 168, pp. 650-653, 2016.

[13] H. Wang et al., "Design and Characterization of Tri-Axis Soft Inductive Tactile Sensors," *IEEE Sens. J.*, vol. 18, no. 19, pp. 7793-7801, 2018.

[14] D. Jones, H. Wang, A. Alazmani, and P. R. Culmer, "A soft multi-axial force sensor to assess tissue properties in RealTime," *IEEE Int. Conf. Intell. Robot. Syst.*, vol. 2017-September, pp. 5738-5743, 2017.

[15] J. Lee, S. Pyo, and M. Kim, "Multidirectional fl exible force sensors based on con fi ned, self-adjusting carbon nanotube arrays."

[16] S. Pyo et al., "Development of a flexible three-axis tactile sensor based on screen-printed carbon nanotube-polymer composite," *J. Micromechanics Microengineering*, vol. 24, no. 7, 2014.

[17] J. Zhang et al., "Highly sensitive flexible three-axis tactile sensors based on the interface contact resistance of microstructured graphene," *Nanoscale*, vol. 10, no. 16, pp. 7387-7395, 2018.

[18] Y. Jung, D. G. Lee, J. Park, H. Ko, and H. Lim, "Piezoresistive tactile sensor discriminating multidirectional forces," *Sensors (Switzerland)*, vol. 15, no. 10, pp. 25463-25473, 2015.

[19] and K. S. Tao Liu, Yoshio Inoue, "A Small and Low-Cost 3-D Tactile Sensor for a Wearable Force Plate," *IEEE Sens. J.*, vol. 9, no. 9, pp. 1103-1110, 2009.

[20] T. Zhang, H. Liu, L. Jiang, S. Fan, and J. Yang, "Development of a flexible 3-D tactile sensor system for anthropomorphic artificial hand," *IEEE Sens. J.*, vol. 13, no. 2, pp. 510-518, 2013.

[21] T. Zhang, L. Jiang, X. Wu, W. Feng, D. Zhou, and H. Liu, "Fingertip Three-Axis Tactile Sensor for Multifingered Grasping," *IEEE/ASME Trans. Mechatronics*, vol. 20, no. 4, pp. 1875-1885, 2015.

The invention claimed is:

1. A compliant tri-axial force sensor comprising:
a first electrode layer having an array of column electrodes in a first orientation;
a second electrode layer having an array of column electrodes in a second orientation, which is orthogonal to the first orientation;
a force-dependent active layer which is configured to change at least one property when subjected to a force and which is provided between the first electrode layer and the second electrode layer;
at least one three dimensional bump arranged to transmit externally applied force through the force-dependent active layer;
wherein at least one spacer is provided which is arranged to maintain a separation between two or more layers in the compliant tri-axial force sensor until an external force is applied; and
wherein the at least one spacer takes the form of a binder provided between the force-dependent active layer and the first and/or second electrode layer, wherein the binder is provided in gaps between adjacent column electrodes and extends between the force-dependent active layer and respective edges of said adjacent column electrodes; or wherein the force-dependent active layer comprises a first active layer and a second active layer with a gap there-between, and wherein the at least one spacer is provided within the force-dependent active layer.

2. The compliant tri-axial force sensor according to claim 1 wherein the force-dependent active layer comprises at least one of: a quantum tunneling material, a piezoresistive material or a piezoelectric material.

3. The compliant tri-axial force sensor according to claim 1 wherein the at least one property is: quantum tunnelling; conductivity; resistivity or electrical charge.

4. The compliant tri-axial force sensor according to claim 1 wherein the at least one three dimensional bump has a footprint which extends at least partially over at least two column electrodes in the first electrode layer and at least partially over at least two column electrodes in the second electrode layer such that forces applied to the at least one three dimensional bump are transmittable through the force-dependent active layer in at least four discrete regions.

5. The compliant tri-axial force sensor according to claim 1 wherein the at least one three dimensional bump has a footprint contained within a space between two adjacent column electrodes in the first electrode layer and between two adjacent column electrodes in the second electrode layer.

6. The compliant tri-axial force sensor according to claim 1 further comprising one or more of: a base layer below the first electrode layer; a top layer above the second electrode layer; a first carbon layer between the first electrode layer and the force-dependent active layer; a second carbon layer between the second electrode layer and the force-dependent active layer; and a cover layer over the at least one three dimensional bump; optionally,
wherein the first and/or second carbon layer is continuous across multiple column electrodes in the first and/or second electrode layer.

7. The compliant tri-axial force sensor according to claim 1 wherein the at least one spacer is provided between a base layer and a top layer; or on or through the first or second electrode layer; and/or
wherein the at least one spacer is in the form of a dot, a column, a post, a cylinder, a tubular, a pyramid, or a mesh; and/or
wherein the at least one spacer has a solid or hollow transverse cross-section in the form of a circle, square, rectangle, diamond, pentagon, hexagon, or honeycomb lattice.

8. The compliant tri-axial force sensor according to claim 1 wherein the at least one spacer comprises an array of said spacers;
optionally, wherein the spacers in the array have a plurality of different dimensions.

9. The compliant tri-axial force sensor according to claim 1 wherein the force-dependent active layer forms a continuous layer across multiple column electrodes in the first and/or second electrode layer; or wherein the force-dependent active layer forms a discontinuous layer across the column electrodes in the first and/or second electrode layer.

10. The compliant tri-axial force sensor according to claim 1 wherein an insulator is provided between adjacent electrodes in the first and/or second electrode layer.

11. The compliant tri-axial force sensor according to claim 1 wherein an adhesive layer is provided between one or more adjacent layers.

12. The compliant tri-axial force sensor according to claim 1 wherein the at least one three dimensional bump comprises a polymer having a different elasticity to a remainder of the compliant tri-axial force sensor.

13. The compliant tri-axial force sensor according to claim 1 wherein the at least one three dimensional bump is in the form of a mesa, dome, hemisphere, hemispherical section, cone, cone section, cuboid, cylinder, half-cylinder, pyramid, pyramid section, tetrahedron, tetrahedron section, hexahedron, triangular prism, or polyhedron.

14. The compliant tri-axial force sensor according to claim 1 wherein the at least one three dimensional bump has a height that is at least twice a height of a remainder of the compliant tri-axial force sensor.

15. The compliant tri-axial force sensor according to claim 1 wherein the at least one three dimensional bump comprises an array of said three dimensional bumps.

* * * * *